US009681951B2

(12) United States Patent
Ratz et al.

(10) Patent No.: US 9,681,951 B2
(45) Date of Patent: Jun. 20, 2017

(54) PROSTHESIS WITH OUTER SKIRT AND ANCHORS

(71) Applicant: Edwards Lifesciences CardiAQ LLC, Irvine, CA (US)

(72) Inventors: J. Brent Ratz, Winchester, MA (US); Arshad Quadri, West Hartford, CT (US); Luca Pesce, Huntington Beach, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 14/197,639

(22) Filed: Mar. 5, 2014

(65) Prior Publication Data

US 2014/0277422 A1   Sep. 18, 2014

Related U.S. Application Data

(60) Provisional application No. 61/789,783, filed on Mar. 15, 2013, provisional application No. 61/782,707, filed on Mar. 14, 2013.

(51) Int. Cl.
*A61F 2/24* (2006.01)
(52) U.S. Cl.
CPC .......... *A61F 2/2418* (2013.01); *A61F 2/2409* (2013.01); *A61F 2/2457* (2013.01); *A61F 2220/0025* (2013.01); *A61F 2230/0041* (2013.01); *A61F 2230/0065* (2013.01)
(58) Field of Classification Search
CPC ................................ A61F 2/2409; A61F 2/24
See application file for complete search history.

(56) References Cited

U.S. PATENT DOCUMENTS

| 1,306,391 | A | 6/1919 | Romanoff |
| 3,312,237 | A | 4/1967 | Mon et al. |
| 3,657,744 | A | 4/1972 | Ersek |
| 3,671,979 | A | 6/1972 | Moulopoulos |
| 3,739,402 | A | 6/1973 | Cooley et al. |

(Continued)

FOREIGN PATENT DOCUMENTS

| CA | 2304325 | 5/2008 |
| CA | 2 827 556 A1 | 7/2012 |

(Continued)

OTHER PUBLICATIONS

US 8,062,357, 11/2011, Salahieh et al. (withdrawn)

(Continued)

*Primary Examiner* — Thomas J Sweet
*Assistant Examiner* — Wade P Schutte
(74) *Attorney, Agent, or Firm* — Knobbe Martens Olson & Bear LLP

(57) ABSTRACT

A prosthesis can be configured to grasp intralumenal tissue when deployed within a body cavity and prevent axial flow of fluid around an exterior of the prosthesis. The prosthesis can include an expandable frame configured to radially expand and contract for deployment within the body cavity, and an outer skirt positioned annularly around an exterior of the expandable frame. In some embodiments, the outer skirt can extend outward from the frame and be secured to an outwardly extending anchor on the frame to create an axial barrier to fluid flow exterior to the frame when deployed within the body cavity.

25 Claims, 5 Drawing Sheets

(56) References Cited

U.S. PATENT DOCUMENTS

| | | |
|---|---|---|
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,908,028 A | 3/1990 | Colon et al. |
| 4,950,227 A | 8/1990 | Savin et al. |
| 4,994,077 A | 2/1991 | Dobben |
| 5,049,154 A | 9/1991 | Quadri |
| 5,067,957 A | 11/1991 | Jervis |
| 5,133,725 A | 7/1992 | Quadri |
| 5,197,978 A | 3/1993 | Hess |
| 5,282,826 A | 2/1994 | Quadri |
| 5,326,371 A | 7/1994 | Love et al. |
| 5,332,402 A | 7/1994 | Teitelbaum |
| 5,344,427 A | 9/1994 | Cottenceau et al. |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,449,385 A | 9/1995 | Religa et al. |
| 5,474,563 A | 12/1995 | Myler et al. |
| 5,509,930 A | 4/1996 | Love |
| 5,545,214 A | 8/1996 | Stevens |
| 5,554,185 A | 9/1996 | Block et al. |
| 5,575,818 A | 11/1996 | Pinchuk |
| 5,607,444 A | 3/1997 | Lam |
| 5,607,469 A | 3/1997 | Frey |
| 5,669,919 A | 9/1997 | Sanders et al. |
| 5,697,382 A | 12/1997 | Love et al. |
| D390,957 S | 2/1998 | Fontaine |
| 5,713,952 A | 2/1998 | Vanney et al. |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,840,081 A | 11/1998 | Andersen et al. |
| 5,855,601 A | 1/1999 | Bessler et al. |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuchi et al. |
| 5,902,334 A | 5/1999 | Dwyer et al. |
| 5,935,108 A | 8/1999 | Katoh et al. |
| 5,954,764 A | 9/1999 | Parodi |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt |
| 6,168,614 B1 | 1/2001 | Andersen et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,309,416 B1 | 10/2001 | Swanson et al. |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,409,759 B1 | 6/2002 | Peredo |
| 6,425,916 B1 | 7/2002 | Garrison et al. |
| 6,440,163 B1 | 8/2002 | Swanson et al. |
| 6,440,164 B1 | 8/2002 | DeMatteo et al. |
| 6,454,799 B1 | 9/2002 | Schreck |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,517,573 B1 | 2/2003 | Pollock et al. |
| 6,527,800 B1 | 3/2003 | McGuckin, Jr. et al. |
| 6,533,812 B2 | 3/2003 | Swanson et al. |
| 6,551,303 B1 | 4/2003 | Van Tassel et al. |
| 6,582,462 B1 | 6/2003 | Andersen et al. |
| 6,602,281 B1 | 8/2003 | Klein |
| 6,610,088 B1 | 8/2003 | Gabbay |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin et al. |
| 6,682,537 B2 | 1/2004 | Ouriel et al. |
| 6,695,878 B2 | 2/2004 | McGuckin et al. |
| 6,712,836 B1 | 3/2004 | Berg et al. |
| 6,723,123 B1 | 4/2004 | Kazatchkov et al. |
| 6,730,118 B2 | 5/2004 | Spenser et al. |
| 6,733,523 B2 | 5/2004 | Shaolian et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,830,584 B1 | 12/2004 | Sequin |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | McGuckin, Jr. et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,960,219 B2 | 11/2005 | Grudem et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,134 B2 | 5/2006 | Khairkhahan et al. |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,147,663 B1 | 12/2006 | Berg et al. |
| 7,153,322 B2 | 12/2006 | Alt |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,232,449 B2 | 6/2007 | Sharkawy et al. |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |
| 7,328,270 B1 | 2/2008 | Reents et al. |
| 7,329,278 B2 | 2/2008 | Seguin et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,422,602 B2 | 9/2008 | Grudem et al. |
| 7,425,219 B2 | 9/2008 | Quadri |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |

(56) References Cited

U.S. PATENT DOCUMENTS

| | | |
|---|---|---|
| 7,524,330 B2 | 4/2009 | Berreklouw |
| 7,527,646 B2 | 5/2009 | Rahdert et al. |
| 7,534,261 B2 | 5/2009 | Friedman |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,618,447 B2 | 11/2009 | Case et al. |
| 7,628,805 B2 | 12/2009 | Spenser et al. |
| 7,632,298 B2 | 12/2009 | Hijlkema et al. |
| 7,682,390 B2 | 3/2010 | Seguin |
| 7,708,775 B2 | 5/2010 | Rowe et al. |
| 7,712,606 B2 | 5/2010 | Salahieh et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,771,472 B2 | 8/2010 | Hendricksen et al. |
| 7,780,725 B2 | 8/2010 | Haug et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |
| 7,815,589 B2 | 10/2010 | Meade et al. |
| 7,815,673 B2 | 10/2010 | Bloom et al. |
| 7,824,443 B2 | 11/2010 | Salahieh et al. |
| 7,837,727 B2 | 11/2010 | Goetz et al. |
| 7,846,203 B2 | 12/2010 | Cribier |
| 7,871,435 B2 | 1/2011 | Carpentier et al. |
| 7,892,281 B2 | 2/2011 | Seguin et al. |
| D635,261 S | 3/2011 | Rossi |
| D635,262 S | 3/2011 | Rossi |
| 7,896,915 B2 | 3/2011 | Guyenot et al. |
| 7,914,569 B2 | 3/2011 | Nguyen et al. |
| 7,919,112 B2 | 4/2011 | Pathak et al. |
| 7,947,075 B2 | 5/2011 | Goetz et al. |
| 7,959,672 B2 | 6/2011 | Salahieh et al. |
| 7,967,853 B2 | 6/2011 | Eidenschink et al. |
| 7,972,377 B2 | 7/2011 | Lane |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 7,993,395 B2 | 8/2011 | Vanermen et al. |
| 7,998,196 B2 | 8/2011 | Mathison |
| 8,009,887 B2 | 8/2011 | Ionasec et al. |
| 8,016,870 B2 | 9/2011 | Chew et al. |
| 8,016,877 B2 | 9/2011 | Seguin et al. |
| 8,029,564 B2 | 10/2011 | Johnson et al. |
| 8,048,153 B2 | 11/2011 | Salahieh et al. |
| 8,052,747 B2 | 11/2011 | Melnikov et al. |
| 8,052,750 B2 | 11/2011 | Tuval et al. |
| 8,057,538 B2 | 11/2011 | Bergin et al. |
| 8,057,539 B2 | 11/2011 | Ghione et al. |
| 8,057,540 B2 | 11/2011 | Letac et al. |
| 8,062,350 B2 | 11/2011 | Gale et al. |
| 8,062,359 B2 | 11/2011 | Marquez et al. |
| 8,066,763 B2 | 11/2011 | Alt |
| 8,070,799 B2 | 12/2011 | Righini et al. |
| 8,070,800 B2 | 12/2011 | Lock et al. |
| 8,070,801 B2 | 12/2011 | Cohn |
| 8,070,802 B2 | 12/2011 | Lamphere et al. |
| 8,075,611 B2 | 12/2011 | Millwee et al. |
| 8,075,615 B2 | 12/2011 | Eberhardt et al. |
| 8,078,279 B2 | 12/2011 | Dennis et al. |
| 8,080,054 B2 | 12/2011 | Rowe |
| 8,083,793 B2 | 12/2011 | Lane et al. |
| 8,088,158 B2 | 1/2012 | Brodeur |
| 8,088,404 B2 | 1/2012 | Udipi et al. |
| 8,092,520 B2 | 1/2012 | Quadri |
| 8,100,964 B2 | 1/2012 | Spence |
| 8,105,375 B2 | 1/2012 | Navia et al. |
| 8,105,377 B2 | 1/2012 | Liddicoat |
| 8,109,995 B2 | 2/2012 | Paniagua et al. |
| 8,109,996 B2 | 2/2012 | Stacchino et al. |
| 8,114,154 B2 | 2/2012 | Righini et al. |
| 8,118,866 B2 | 2/2012 | Herrmann et al. |
| 8,119,704 B2 | 2/2012 | Wang et al. |
| 8,123,801 B2 | 2/2012 | Milo |
| 8,128,681 B2 | 3/2012 | Shoemaker et al. |
| 8,128,688 B2 | 3/2012 | Ding et al. |
| 8,136,218 B2 | 3/2012 | Millwee et al. |
| 8,137,398 B2 | 3/2012 | Tuval et al. |
| 8,137,687 B2 | 3/2012 | Chen et al. |
| 8,142,492 B2 | 3/2012 | Forster et al. |
| 8,142,494 B2 | 3/2012 | Rahdert et al. |
| 8,147,504 B2 | 4/2012 | Ino et al. |
| 8,155,754 B2 | 4/2012 | Nygren et al. |
| 8,157,852 B2 | 4/2012 | Bloom et al. |
| 8,157,853 B2 | 4/2012 | Laske et al. |
| 8,158,187 B2 | 4/2012 | Chen et al. |
| 8,163,014 B2 | 4/2012 | Lane et al. |
| 8,167,926 B2 | 5/2012 | Hartley et al. |
| 8,167,932 B2 | 5/2012 | Bourang et al. |
| 8,167,934 B2 | 5/2012 | Styrc et al. |
| 8,168,275 B2 | 5/2012 | Lee et al. |
| 8,170,645 B2 | 5/2012 | Solar et al. |
| 8,177,799 B2 | 5/2012 | Orban, III |
| 8,177,836 B2 | 5/2012 | Lee et al. |
| 8,180,428 B2 | 5/2012 | Kaiser et al. |
| 8,182,528 B2 | 5/2012 | Salahieh et al. |
| 8,182,530 B2 | 5/2012 | Huber |
| 8,182,829 B2 | 5/2012 | Kleiner et al. |
| 8,187,319 B2 | 5/2012 | Zilla et al. |
| 8,187,851 B2 | 5/2012 | Shah et al. |
| 8,195,293 B2 | 6/2012 | Limousin et al. |
| 8,202,529 B2 | 6/2012 | Hossainy et al. |
| 8,211,169 B2 | 7/2012 | Lane et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| 8,221,493 B2 | 7/2012 | Boyle et al. |
| 8,226,710 B2 | 7/2012 | Nguyen et al. |
| 8,231,930 B2 | 7/2012 | Castro et al. |
| D665,079 S | 8/2012 | Zago |
| D665,080 S | 8/2012 | Zago |
| 8,236,045 B2 | 8/2012 | Benichou et al. |
| 8,236,241 B2 | 8/2012 | Carpentier et al. |
| 8,241,274 B2 | 8/2012 | Keogh et al. |
| 8,246,675 B2 | 8/2012 | Zegdi |
| 8,246,677 B2 | 8/2012 | Ryan |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,257,724 B2 | 9/2012 | Cromack et al. |
| 8,257,725 B2 | 9/2012 | Cromack et al. |
| 8,262,724 B2 | 9/2012 | Seguin et al. |
| 8,273,118 B2 | 9/2012 | Bergin |
| 8,273,120 B2 | 9/2012 | Dolan |
| 8,276,533 B2 | 10/2012 | Chambers et al. |
| 8,287,584 B2 | 10/2012 | Salahieh et al. |
| 8,287,591 B2 | 10/2012 | Keidar et al. |
| 8,292,948 B2 | 10/2012 | Mauch et al. |
| 8,303,653 B2 | 11/2012 | Bonhoeffer et al. |
| 8,308,798 B2 | 11/2012 | Pintor et al. |
| 8,313,520 B2 | 11/2012 | Barbut et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,323,336 B2 | 12/2012 | Hill et al. |
| 8,323,678 B2 | 12/2012 | Wang et al. |
| 8,337,541 B2 | 12/2012 | Quadri et al. |
| 8,348,995 B2 | 1/2013 | Tuval et al. |
| 8,349,001 B2 | 1/2013 | Mensah et al. |
| 8,349,003 B2 | 1/2013 | Shu et al. |
| 8,353,921 B2 | 1/2013 | Schaller et al. |
| 8,353,948 B2 | 1/2013 | Besselink et al. |
| 8,353,953 B2 | 1/2013 | Giannetti et al. |
| 8,357,195 B2 | 1/2013 | Kuehn |
| 8,357,387 B2 | 1/2013 | Dove et al. |
| 8,361,137 B2 | 1/2013 | Perouse |

(56) References Cited

U.S. PATENT DOCUMENTS

| | | |
|---|---|---|
| 8,361,537 B2 | 1/2013 | Shanley |
| 8,366,769 B2 | 2/2013 | Huynh et al. |
| 8,374,692 B2 | 2/2013 | Bobgan et al. |
| 8,377,115 B2 | 2/2013 | Thompson |
| 8,377,116 B2 | 2/2013 | Hsu et al. |
| 8,377,499 B2 | 2/2013 | Kleiner et al. |
| 8,382,816 B2 | 2/2013 | Pollock et al. |
| RE44,075 E | 3/2013 | Williamson et al. |
| 8,398,707 B2 | 3/2013 | Bergin |
| 8,398,708 B2 | 3/2013 | Meiri et al. |
| 8,403,983 B2 | 3/2013 | Quadri et al. |
| 8,408,214 B2 | 4/2013 | Spenser |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,430,902 B2 | 4/2013 | Bergheim |
| 8,430,927 B2 | 4/2013 | Bonhoeffer |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,684 B2 | 6/2013 | Bergin et al. |
| 8,454,685 B2 | 6/2013 | Hariton et al. |
| 8,460,335 B2 | 6/2013 | Carpenter |
| 8,460,365 B2 | 6/2013 | Haverkost et al. |
| 8,460,366 B2 | 6/2013 | Rowe |
| 8,460,370 B2 | 6/2013 | Zakay et al. |
| 8,460,373 B2 | 6/2013 | Fogarty et al. |
| 8,465,541 B2 | 6/2013 | Dwork |
| 8,470,023 B2 | 6/2013 | Eidenschink et al. |
| 8,470,024 B2 | 6/2013 | Ghione et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,491,650 B2 | 7/2013 | Wiemeyer et al. |
| 8,500,688 B2 | 8/2013 | Engel et al. |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Alkhatib |
| 8,512,399 B2 | 8/2013 | Lafontaine |
| 8,512,400 B2 | 8/2013 | Tran et al. |
| 8,512,401 B2 | 8/2013 | Murray, III et al. |
| 8,518,106 B2 | 8/2013 | Duffy et al. |
| 8,518,107 B2 | 8/2013 | Tsukashima |
| 8,518,108 B2 | 8/2013 | Huynh et al. |
| 8,523,940 B2 | 9/2013 | Richardson et al. |
| 8,529,621 B2 | 9/2013 | Alfieri et al. |
| 8,532,769 B2 | 9/2013 | Kornet et al. |
| 8,535,368 B2 | 9/2013 | Headley, Jr. et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,556,966 B2 | 10/2013 | Jenson |
| 8,562,663 B2 | 10/2013 | Mearns et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,568,474 B2 | 10/2013 | Yeung et al. |
| 8,568,475 B2 | 10/2013 | Nguyen et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,584,849 B2 | 11/2013 | McCaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,597,348 B2 | 12/2013 | Rowe et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,617,236 B2 | 12/2013 | Paul et al. |
| 8,617,379 B2 | 12/2013 | Wong et al. |
| 8,623,074 B2 | 1/2014 | Ryan |
| 8,623,075 B2 | 1/2014 | Murray, III et al. |
| 8,623,079 B2 | 1/2014 | Savage et al. |
| 8,623,080 B2 | 1/2014 | Fogarty et al. |
| 8,628,566 B2 | 1/2014 | Eberhardt et al. |
| 8,632,586 B2 | 1/2014 | Spenser |
| 8,632,608 B2 | 1/2014 | Carpentier et al. |
| 8,634,911 B2 | 1/2014 | Stegemann et al. |
| 8,640,521 B2 | 2/2014 | Righini et al. |
| 8,641,639 B2 | 2/2014 | Manstrom et al. |
| 8,641,757 B2 | 2/2014 | Pintor et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri |
| 8,652,204 B2 | 2/2014 | Quill et al. |
| 8,653,632 B2 | 2/2014 | Pederson et al. |
| 8,657,872 B2 | 2/2014 | Seguin |
| 8,663,305 B2 | 3/2014 | Argentine |
| 8,663,318 B2 | 3/2014 | Ho |
| 8,663,319 B2 | 3/2014 | Ho |
| 8,668,730 B2 | 3/2014 | Mcguckin, Jr. et al. |
| 8,668,733 B2 | 3/2014 | Haug et al. |
| 8,672,992 B2 | 3/2014 | Orr |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,678,033 B2 | 3/2014 | Bengea et al. |
| 8,679,174 B2 | 3/2014 | Ottma et al. |
| 8,679,404 B2 | 3/2014 | Liburd et al. |
| 8,685,083 B2 | 4/2014 | Perier et al. |
| 8,685,084 B2 | 4/2014 | Rolando et al. |
| 8,685,086 B2 | 4/2014 | Navia et al. |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,696,743 B2 | 4/2014 | Holecek et al. |
| 8,707,957 B2 | 4/2014 | Callister et al. |
| 8,715,207 B2 | 5/2014 | Righini et al. |
| 8,715,337 B2 | 5/2014 | Chuter |
| 8,715,343 B2 | 5/2014 | Navia et al. |
| 8,718,765 B2 | 5/2014 | Baumann et al. |
| 8,721,707 B2 | 5/2014 | Boucher et al. |
| 8,721,708 B2 | 5/2014 | Sequin et al. |
| 8,721,713 B2 | 5/2014 | Tower et al. |
| 8,721,714 B2 | 5/2014 | Kelley |
| 8,721,715 B2 | 5/2014 | Wang |
| 8,728,154 B2 * | 5/2014 | Alkhatib ..................... 623/2.17 |
| 8,728,155 B2 | 5/2014 | Montorfano et al. |
| 8,731,658 B2 | 5/2014 | Hampton et al. |
| 8,734,484 B2 | 5/2014 | Ahlberg et al. |
| 8,740,930 B2 | 6/2014 | Goodwin |
| 8,740,974 B2 | 6/2014 | Lambrecht et al. |
| 8,740,975 B2 | 6/2014 | Yang et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,753,393 B2 | 6/2014 | Strasly et al. |
| 8,758,432 B2 | 6/2014 | Solem |
| 8,764,814 B2 | 7/2014 | Solem |
| 8,764,818 B2 | 7/2014 | Gregg |
| 8,764,820 B2 | 7/2014 | Dehdashtian et al. |

(56) References Cited

U.S. PATENT DOCUMENTS

| | | |
|---|---|---|
| 8,771,302 B2 | 7/2014 | Woolfson et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,966 B2 | 7/2014 | Dale et al. |
| 8,777,975 B2 | 7/2014 | Kashkarov et al. |
| 8,778,018 B2 | 7/2014 | Iobbi |
| 8,778,019 B2 | 7/2014 | Knippel et al. |
| 8,778,020 B2 | 7/2014 | Gregg et al. |
| 8,784,477 B2 | 7/2014 | Bregulla et al. |
| 8,784,478 B2 | 7/2014 | Tuval et al. |
| 8,784,480 B2 | 7/2014 | Taylor et al. |
| 8,784,481 B2 | 7/2014 | Alkhatib et al. |
| 8,790,387 B2 | 7/2014 | Nguyen et al. |
| 8,790,395 B2 | 7/2014 | Straubinger et al. |
| 8,790,396 B2 | 7/2014 | Bergheim et al. |
| 8,791,171 B2 | 7/2014 | Pacetti |
| 8,795,354 B2 | 8/2014 | Benichou et al. |
| 8,795,356 B2 | 8/2014 | Quadri et al. |
| 8,795,357 B2 | 8/2014 | Yohanan et al. |
| 8,798,771 B2 | 8/2014 | Casset et al. |
| 8,801,776 B2 | 8/2014 | House et al. |
| 8,808,366 B2 | 8/2014 | Braido et al. |
| 8,808,370 B2 | 8/2014 | Nitzan et al. |
| 8,814,931 B2 | 8/2014 | Wang et al. |
| 8,821,569 B2 | 9/2014 | Gurskis et al. |
| 8,821,570 B2 | 9/2014 | DuMontelle et al. |
| 8,822,219 B2 | 9/2014 | Strasly et al. |
| 8,828,078 B2 | 9/2014 | Salahieh et al. |
| 8,828,079 B2 | 9/2014 | Thielen et al. |
| 8,834,349 B2 | 9/2014 | Waisblatt et al. |
| 8,834,561 B2 | 9/2014 | Figulla et al. |
| 8,834,563 B2 | 9/2014 | Righini |
| 8,834,564 B2 | 9/2014 | Tuval et al. |
| 8,839,957 B2 | 9/2014 | Murad et al. |
| 8,840,661 B2 | 9/2014 | Manasse |
| 8,840,664 B2 | 9/2014 | Karapetian et al. |
| 8,844,365 B2 | 9/2014 | Gregg et al. |
| 8,845,718 B2 | 9/2014 | Tuval et al. |
| 8,845,720 B2 | 9/2014 | Conklin |
| 8,846,390 B2 | 9/2014 | Dove et al. |
| 8,851,286 B2 | 10/2014 | Chang et al. |
| 8,858,620 B2 | 10/2014 | Salahieh et al. |
| 8,858,621 B2 | 10/2014 | Oba et al. |
| 8,869,982 B2 | 10/2014 | Hodshon et al. |
| 8,870,936 B2 | 10/2014 | Rowe |
| 8,870,947 B2 | 10/2014 | Shaw |
| 8,870,948 B1 | 10/2014 | Erzberger et al. |
| 8,876,712 B2 | 11/2014 | Yee et al. |
| 8,876,883 B2 | 11/2014 | Rust |
| 8,876,892 B2 | 11/2014 | Tran et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,882,831 B2 | 11/2014 | Alkhatib |
| 8,888,709 B2 | 11/2014 | Shuros et al. |
| 8,888,730 B2 | 11/2014 | Rossi et al. |
| 8,888,794 B2 | 11/2014 | Hausen |
| 8,888,838 B2 | 11/2014 | Blanzy |
| 8,894,702 B2 | 11/2014 | Quadri et al. |
| 8,894,703 B2 | 11/2014 | Salahieh et al. |
| 8,900,295 B2 | 12/2014 | Migliazza et al. |
| 8,900,862 B2 | 12/2014 | Alavi et al. |
| 8,906,081 B2 | 12/2014 | Cully et al. |
| 8,906,601 B2 | 12/2014 | Dove et al. |
| 8,911,455 B2 | 12/2014 | Quadri et al. |
| 8,911,490 B2 | 12/2014 | Perkins et al. |
| 8,911,844 B2 | 12/2014 | Ford |
| 8,915,960 B2 | 12/2014 | Carpentier et al. |
| 8,918,192 B2 | 12/2014 | Ollivier et al. |
| 8,923,963 B2 | 12/2014 | Bonner et al. |
| 8,926,688 B2 | 1/2015 | Burkart et al. |
| 8,926,690 B2 | 1/2015 | Kovalsky |
| 8,926,692 B2 | 1/2015 | Dwork |
| 8,926,693 B2 | 1/2015 | Duffy et al. |
| 8,926,694 B2 | 1/2015 | Costello |
| 8,932,343 B2 | 1/2015 | Alkhatib et al. |
| 8,932,349 B2 | 1/2015 | Jenson et al. |
| 8,932,350 B2 | 1/2015 | Brunnett et al. |
| 8,936,650 B2 | 1/2015 | Alavi et al. |
| 8,940,014 B2 | 1/2015 | Gamarra et al. |
| 8,940,887 B2 | 1/2015 | Chatterton et al. |
| 8,945,208 B2 | 2/2015 | Jimenez et al. |
| 8,945,209 B2 | 2/2015 | Bonyuet et al. |
| 8,945,210 B2 | 2/2015 | Cartledge et al. |
| 8,945,212 B2 | 2/2015 | Bruchman et al. |
| 8,951,243 B2 | 2/2015 | Crisostomo et al. |
| 8,951,280 B2 | 2/2015 | Cohn et al. |
| 8,951,299 B2 | 2/2015 | Paul et al. |
| 8,956,404 B2 | 2/2015 | Bortlein et al. |
| 8,956,405 B2 | 2/2015 | Wang et al. |
| 8,961,583 B2 | 2/2015 | Hojeibane et al. |
| 8,961,589 B2 | 2/2015 | Kleiner et al. |
| 8,961,593 B2 | 2/2015 | Bonhoeffer et al. |
| 8,961,594 B2 | 2/2015 | Maisano et al. |
| 8,961,595 B2 | 2/2015 | Alkhatib |
| 8,961,599 B2 | 2/2015 | Bruchman et al. |
| 8,966,868 B2 | 3/2015 | Wang et al. |
| 8,968,336 B2 | 3/2015 | Conklin et al. |
| 8,968,393 B2 | 3/2015 | Rothstein |
| 8,968,394 B2 | 3/2015 | Murad et al. |
| 8,968,395 B2 | 3/2015 | Hauser et al. |
| 8,973,234 B2 | 3/2015 | Johnson et al. |
| 8,974,475 B2 | 3/2015 | Rothstein et al. |
| 8,974,524 B2 | 3/2015 | Yeung et al. |
| 8,979,922 B2 | 3/2015 | Jayasinghe et al. |
| 8,980,176 B2 | 3/2015 | Reggiani et al. |
| 8,986,320 B2 | 3/2015 | Maimon et al. |
| 8,986,371 B2 | 3/2015 | Quill et al. |
| 8,986,372 B2 | 3/2015 | Murry, III et al. |
| 8,986,374 B2 | 3/2015 | Cao et al. |
| 8,986,375 B2 | 3/2015 | Garde et al. |
| 8,986,713 B2 | 3/2015 | Cleek et al. |
| 8,992,608 B2 | 3/2015 | Haug et al. |
| 8,992,761 B2 | 3/2015 | Lin |
| 8,998,976 B2 | 4/2015 | Gregg et al. |
| 8,998,978 B2 | 4/2015 | Wang |
| 8,998,979 B2 | 4/2015 | Seguin et al. |
| 8,998,980 B2 | 4/2015 | Shipley et al. |
| 8,998,981 B2 | 4/2015 | Tuval et al. |
| 8,999,369 B2 | 4/2015 | Gale et al. |
| 9,005,270 B2 | 4/2015 | Perkins et al. |
| 9,005,273 B2 | 4/2015 | Salahieh et al. |
| 9,005,277 B2 | 4/2015 | Pintor et al. |
| 9,005,279 B2 | 4/2015 | Gabbay |
| 9,011,521 B2 | 4/2015 | Haug et al. |
| 9,011,523 B2 | 4/2015 | Seguin |
| 9,011,524 B2 | 4/2015 | Eberhardt |
| 9,011,528 B2 | 4/2015 | Ryan |
| 9,021,674 B2 | 5/2015 | Hillukka et al. |
| 9,023,100 B2 | 5/2015 | Quadri et al. |
| 9,028,545 B2 | 5/2015 | Taylor |
| 9,029,418 B2 | 5/2015 | Dove et al. |
| 9,033,887 B2 | 5/2015 | Ionasec et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,044,221 B2 | 6/2015 | Zentgraf et al. |
| 9,055,937 B2 | 6/2015 | Rowe et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 2001/0007956 A1 | 7/2001 | Letac et al. |
| 2001/0021872 A1 | 9/2001 | Bailey et al. |
| 2001/0047180 A1 | 11/2001 | Grudem et al. |
| 2001/0047200 A1 | 11/2001 | White et al. |
| 2002/0016623 A1 | 2/2002 | Kula et al. |
| 2002/0022853 A1 | 2/2002 | Swanson et al. |
| 2002/0032481 A1 | 3/2002 | Gabbay |
| 2002/0045929 A1 | 4/2002 | Diaz |
| 2002/0052644 A1 | 5/2002 | Shaolian et al. |

(56) References Cited

U.S. PATENT DOCUMENTS

| | | |
|---|---|---|
| 2002/0055772 A1 | 5/2002 | McGuckin et al. |
| 2002/0077695 A1 | 6/2002 | Swanson et al. |
| 2002/0111619 A1 | 8/2002 | Keast et al. |
| 2002/0111647 A1 | 8/2002 | Khairkhahan et al. |
| 2002/0183827 A1 | 12/2002 | Derus et al. |
| 2003/0014104 A1 | 1/2003 | Cribier |
| 2003/0040792 A1 | 2/2003 | Gabbay |
| 2003/0083679 A1 | 5/2003 | Grudem et al. |
| 2003/0105517 A1 | 6/2003 | White et al. |
| 2003/0109924 A1 | 6/2003 | Cribier |
| 2003/0114913 A1 | 6/2003 | Spenser et al. |
| 2003/0120263 A1 | 6/2003 | Ouriel et al. |
| 2003/0120330 A1 | 6/2003 | Ouriel et al. |
| 2003/0120333 A1 | 6/2003 | Ouriel et al. |
| 2003/0125797 A1 | 7/2003 | Chobotov et al. |
| 2003/0130729 A1 | 7/2003 | Paniagua |
| 2003/0176914 A1 | 9/2003 | Rabkin et al. |
| 2003/0187499 A1 | 10/2003 | Swanson et al. |
| 2003/0199971 A1 | 10/2003 | Tower et al. |
| 2003/0220683 A1 | 11/2003 | Minasian et al. |
| 2004/0039436 A1 | 2/2004 | Spenser et al. |
| 2004/0087900 A1 | 5/2004 | Thompson et al. |
| 2004/0093058 A1 | 5/2004 | Cottone et al. |
| 2004/0093060 A1 | 5/2004 | Seguin et al. |
| 2004/0102842 A1 | 5/2004 | Jansen |
| 2004/0117009 A1 | 6/2004 | Cali et al. |
| 2004/0133273 A1 | 7/2004 | Cox |
| 2004/0186561 A1 | 9/2004 | McGuckin, Jr. et al. |
| 2004/0193261 A1 | 9/2004 | Berreklou |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin, Jr. et al. |
| 2004/0236411 A1 | 11/2004 | Sarac et al. |
| 2004/0243230 A1 | 12/2004 | Navia et al. |
| 2004/0249433 A1 | 12/2004 | Freitag |
| 2004/0260390 A1 | 12/2004 | Sarac et al. |
| 2005/0033398 A1 | 2/2005 | Seguin |
| 2005/0038470 A1 | 2/2005 | van der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137695 A1 | 6/2005 | Salahieh et al. |
| 2005/0137701 A1 | 6/2005 | Salahieh et al. |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203616 A1 | 9/2005 | Cribier |
| 2005/0203618 A1 | 9/2005 | Sharkawy et al. |
| 2005/0216079 A1 | 9/2005 | Macoviak |
| 2005/0234546 A1 | 10/2005 | Nugent et al. |
| 2005/0240204 A1 | 10/2005 | Grudem et al. |
| 2005/0251251 A1 | 11/2005 | Cribier |
| 2005/0283231 A1 | 12/2005 | Haug et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0149360 A1 | 7/2006 | Schwammenthal et al. |
| 2006/0161265 A1 | 7/2006 | Levine et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0010876 A1 | 1/2007 | Salahieh et al. |
| 2007/0016286 A1 | 1/2007 | Herrmann et al. |
| 2007/0043435 A1 | 2/2007 | Seguin et al. |
| 2007/0050021 A1 | 3/2007 | Johnson |
| 2007/0067016 A1 | 3/2007 | Jung |
| 2007/0100432 A1 | 5/2007 | Case et al. |
| 2007/0118206 A1 | 5/2007 | Colgan et al. |
| 2007/0118207 A1 | 5/2007 | Amplatz et al. |
| 2007/0123798 A1 | 5/2007 | Rahamimov |
| 2007/0129794 A1 | 6/2007 | Realyvasquez |
| 2007/0142906 A1 | 6/2007 | Figulla et al. |
| 2007/0162107 A1 | 7/2007 | Haug et al. |
| 2007/0185559 A1 | 8/2007 | Shelso |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0270932 A1 | 11/2007 | Headley et al. |
| 2007/0270937 A1 | 11/2007 | Leanna |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1* | 3/2008 | Tuval et al. ............... 623/2.38 |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097571 A1 | 4/2008 | Denison et al. |
| 2008/0097581 A1 | 4/2008 | Shanley |
| 2008/0114441 A1 | 5/2008 | Rust et al. |
| 2008/0125853 A1 | 5/2008 | Bailey et al. |
| 2008/0125859 A1 | 5/2008 | Salahieh et al. |
| 2008/0133003 A1 | 6/2008 | Seguin et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154358 A1 | 6/2008 | Tansley et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-Muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0243233 A1 | 10/2008 | Ben-Muvhar et al. |
| 2008/0243245 A1 | 10/2008 | Thambar et al. |
| 2008/0255661 A1 | 10/2008 | Straubinger et al. |
| 2008/0262596 A1 | 10/2008 | Xiao |
| 2008/0262603 A1 | 10/2008 | Giaquinta et al. |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288062 A1 | 11/2008 | Andrieu et al. |
| 2008/0319526 A1 | 12/2008 | Hill et al. |
| 2009/0005863 A1 | 1/2009 | Goetz et al. |
| 2009/0012602 A1 | 1/2009 | Quadri |
| 2009/0054976 A1 | 2/2009 | Tuval et al. |
| 2009/0062908 A1 | 3/2009 | Bonhoeffer et al. |
| 2009/0076531 A1 | 3/2009 | Richardson et al. |
| 2009/0076585 A1 | 3/2009 | Hendriksen et al. |
| 2009/0076598 A1 | 3/2009 | Salahieh et al. |
| 2009/0082844 A1 | 3/2009 | Zacharias et al. |

(56) References Cited

U.S. PATENT DOCUMENTS

| | | |
|---|---|---|
| 2009/0082847 A1 | 3/2009 | Zacharias et al. |
| 2009/0088832 A1 | 4/2009 | Chew et al. |
| 2009/0088836 A1 | 4/2009 | Bishop et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0118744 A1 | 5/2009 | Wells et al. |
| 2009/0118824 A1 | 5/2009 | Samkov |
| 2009/0118826 A1 | 5/2009 | Khaghani |
| 2009/0125096 A1 | 5/2009 | Chu et al. |
| 2009/0125104 A1 | 5/2009 | Hoffman |
| 2009/0132035 A1 | 5/2009 | Roth et al. |
| 2009/0132037 A1 | 5/2009 | Hoffman et al. |
| 2009/0138069 A1 | 5/2009 | Hoffman |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf et al. |
| 2009/0171438 A1 | 7/2009 | Chuter et al. |
| 2009/0171456 A1 | 7/2009 | Kveen et al. |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |
| 2009/0216314 A1 | 8/2009 | Quadri |
| 2009/0216317 A1 | 8/2009 | Cromack et al. |
| 2009/0222076 A1 | 9/2009 | Figulla et al. |
| 2009/0227992 A1 | 9/2009 | Nir et al. |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0258958 A1 | 10/2009 | Ford |
| 2009/0264989 A1 | 10/2009 | Bonhoeffer et al. |
| 2009/0264997 A1 | 10/2009 | Salahieh et al. |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2010/0004740 A1 | 1/2010 | Seguin et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0114299 A1 | 5/2010 | Ben Muvhar et al. |
| 2010/0114305 A1 | 5/2010 | Kang et al. |
| 2010/0121461 A1 | 5/2010 | Sobrino-Serrano et al. |
| 2010/0161027 A1 | 6/2010 | Orr |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249908 A1 | 9/2010 | Chau et al. |
| 2010/0256723 A1 | 10/2010 | Murray |
| 2010/0262157 A1 | 10/2010 | Silver et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0022164 A1 | 1/2011 | Quinn et al. |
| 2011/0022165 A1 | 1/2011 | Oba et al. |
| 2011/0022166 A1 | 1/2011 | Dahlgren et al. |
| 2011/0022169 A1 | 1/2011 | Ryan et al. |
| 2011/0029067 A1 | 2/2011 | Mcguckin, Jr. et al. |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0208297 A1 | 8/2011 | Tuval et al. |
| 2011/0218619 A1 | 9/2011 | Benichou et al. |
| 2011/0224780 A1 | 9/2011 | Tabor et al. |
| 2011/0224785 A1 | 9/2011 | Hacohen |
| 2011/0264196 A1 | 10/2011 | Savage et al. |
| 2011/0282438 A1 | 11/2011 | Drews et al. |
| 2011/0282440 A1 | 11/2011 | Cao et al. |
| 2011/0288577 A1 | 11/2011 | Newhauser et al. |
| 2011/0288626 A1 | 11/2011 | Straubinger et al. |
| 2011/0288636 A1 | 11/2011 | Rolando et al. |
| 2011/0295216 A1 | 12/2011 | Miller |
| 2011/0295363 A1 | 12/2011 | Girard et al. |
| 2011/0301702 A1 | 12/2011 | Rust et al. |
| 2011/0301704 A1 | 12/2011 | Alfieri et al. |
| 2011/0313515 A1 | 12/2011 | Quadri et al. |
| 2011/0319981 A1 | 12/2011 | Hill et al. |
| 2011/0319989 A1* | 12/2011 | Lane et al. ................. 623/2.11 |
| 2012/0012487 A1 | 1/2012 | Tian et al. |
| 2012/0016342 A1 | 1/2012 | Brecker |
| 2012/0016411 A1 | 1/2012 | Tuval |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022642 A1 | 1/2012 | Haug et al. |
| 2012/0029627 A1 | 2/2012 | Salahieh et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041550 A1 | 2/2012 | Salahieh et al. |
| 2012/0041551 A1 | 2/2012 | Spenser et al. |
| 2012/0046738 A1 | 2/2012 | Lau et al. |
| 2012/0053514 A1 | 3/2012 | Robinson et al. |
| 2012/0053681 A1 | 3/2012 | Alkhatib et al. |
| 2012/0053682 A1 | 3/2012 | Kovalsky et al. |
| 2012/0059452 A1 | 3/2012 | Boucher et al. |
| 2012/0059454 A1 | 3/2012 | Millwee et al. |
| 2012/0059458 A1 | 3/2012 | Buchbinder et al. |
| 2012/0078237 A1 | 3/2012 | Wang et al. |
| 2012/0078351 A1 | 3/2012 | Klima et al. |
| 2012/0078353 A1 | 3/2012 | Quadri et al. |
| 2012/0078356 A1 | 3/2012 | Fish et al. |
| 2012/0078360 A1 | 3/2012 | Rafiee |
| 2012/0083880 A1 | 4/2012 | Rankin et al. |
| 2012/0095521 A1 | 4/2012 | Hintz |
| 2012/0097178 A1 | 4/2012 | Helm et al. |
| 2012/0101571 A1 | 4/2012 | Thambar et al. |
| 2012/0101572 A1 | 4/2012 | Kovalsky et al. |
| 2012/0123284 A1 | 5/2012 | Kheradvar |
| 2012/0123529 A1 | 5/2012 | Levi et al. |
| 2012/0123557 A1 | 5/2012 | Carpentier et al. |
| 2012/0136200 A1 | 5/2012 | Miraki |
| 2012/0136434 A1 | 5/2012 | Carpentier et al. |
| 2012/0158128 A1 | 6/2012 | Gautam et al. |
| 2012/0158129 A1 | 6/2012 | Duffy et al. |
| 2012/0179051 A1 | 7/2012 | Pfeiffer et al. |
| 2012/0179239 A1 | 7/2012 | Quadri et al. |
| 2012/0179243 A1 | 7/2012 | Yang et al. |
| 2012/0185033 A1 | 7/2012 | Ryan |
| 2012/0185038 A1 | 7/2012 | Fish et al. |
| 2012/0191183 A1 | 7/2012 | Rzany et al. |
| 2012/0197391 A1 | 8/2012 | Alkhatib et al. |
| 2012/0209375 A1 | 8/2012 | Madrid et al. |
| 2012/0215303 A1 | 8/2012 | Quadri et al. |
| 2012/0226340 A1 | 9/2012 | Leschinsky |
| 2012/0239142 A1 | 9/2012 | Liu et al. |
| 2012/0253386 A1 | 10/2012 | Rowe et al. |
| 2012/0259405 A1 | 10/2012 | Weber et al. |
| 2012/0259409 A1 | 10/2012 | Nguyen et al. |
| 2012/0271398 A1 | 10/2012 | Essinger et al. |
| 2012/0271411 A1 | 10/2012 | Duhay et al. |
| 2012/0277850 A1 | 11/2012 | Bertini |
| 2012/0283820 A1 | 11/2012 | Tseng et al. |
| 2012/0283824 A1 | 11/2012 | Lutter et al. |
| 2012/0290062 A1 | 11/2012 | McNamara et al. |
| 2012/0294761 A1 | 11/2012 | Reggiani et al. |
| 2012/0296160 A1 | 11/2012 | Hill et al. |
| 2012/0296418 A1 | 11/2012 | Bonyuet et al. |

(56) References Cited

U.S. PATENT DOCUMENTS

| | | |
|---|---|---|
| 2012/0300063 A1 | 11/2012 | Majkrzak et al. |
| 2012/0303048 A1 | 11/2012 | Manasse |
| 2012/0303116 A1 | 11/2012 | Gorman, III et al. |
| 2012/0305441 A1 | 12/2012 | Murray et al. |
| 2012/0310328 A1 | 12/2012 | Olson et al. |
| 2012/0310330 A1 | 12/2012 | Buchbinder et al. |
| 2012/0310332 A1 | 12/2012 | Murray et al. |
| 2012/0316639 A1 | 12/2012 | Kleinschrodt |
| 2012/0323313 A1 | 12/2012 | Seguin |
| 2012/0323316 A1 | 12/2012 | Chau et al. |
| 2012/0323545 A1 | 12/2012 | Aulbach et al. |
| 2012/0330409 A1 | 12/2012 | Haug et al. |
| 2013/0006294 A1 | 1/2013 | Kashkarov |
| 2013/0012767 A1 | 1/2013 | Nguyen et al. |
| 2013/0018307 A1 | 1/2013 | Lee et al. |
| 2013/0018458 A1* | 1/2013 | Yohanan ............ A61F 2/2418 623/2.18 |
| 2013/0023984 A1 | 1/2013 | Conklin |
| 2013/0030418 A1 | 1/2013 | Taft et al. |
| 2013/0030519 A1 | 1/2013 | Tran et al. |
| 2013/0030520 A1 | 1/2013 | Lee et al. |
| 2013/0030521 A1 | 1/2013 | Nitzan et al. |
| 2013/0030523 A1 | 1/2013 | Padala et al. |
| 2013/0046378 A1 | 2/2013 | Millwee et al. |
| 2013/0053949 A1 | 2/2013 | Pintor et al. |
| 2013/0053950 A1 | 2/2013 | Rowe et al. |
| 2013/0060328 A1 | 3/2013 | Rothstein |
| 2013/0073032 A1 | 3/2013 | Wang |
| 2013/0073037 A1 | 3/2013 | Gregg et al. |
| 2013/0079872 A1 | 3/2013 | Gallagher |
| 2013/0089655 A1 | 4/2013 | Gregg |
| 2013/0090303 A1 | 4/2013 | Mathieu et al. |
| 2013/0090727 A1 | 4/2013 | Forster et al. |
| 2013/0090729 A1 | 4/2013 | Gregg |
| 2013/0091688 A1 | 4/2013 | Goetz et al. |
| 2013/0095264 A1 | 4/2013 | Sowinski et al. |
| 2013/0096664 A1 | 4/2013 | Goetz et al. |
| 2013/0096671 A1 | 4/2013 | Iobbi |
| 2013/0096672 A1 | 4/2013 | Reich et al. |
| 2013/0103131 A1 | 4/2013 | Goetz et al. |
| 2013/0103138 A1 | 4/2013 | Hossainy et al. |
| 2013/0110097 A1 | 5/2013 | Schneider et al. |
| 2013/0110226 A1 | 5/2013 | Gurskis |
| 2013/0110227 A1 | 5/2013 | Quadri et al. |
| 2013/0110230 A1 | 5/2013 | Solem |
| 2013/0116654 A1 | 5/2013 | Dehdashtian et al. |
| 2013/0116676 A1 | 5/2013 | Tian et al. |
| 2013/0116776 A1 | 5/2013 | Gross et al. |
| 2013/0116777 A1 | 5/2013 | Pintor et al. |
| 2013/0116779 A1 | 5/2013 | Weber |
| 2013/0123757 A1 | 5/2013 | Crisostomo et al. |
| 2013/0123796 A1 | 5/2013 | Sutton et al. |
| 2013/0123898 A1 | 5/2013 | Tung et al. |
| 2013/0123912 A1 | 5/2013 | Tung et al. |
| 2013/0131788 A1 | 5/2013 | Quadri et al. |
| 2013/0131793 A1 | 5/2013 | Quadri et al. |
| 2013/0138203 A1 | 5/2013 | Quadri et al. |
| 2013/0138207 A1 | 5/2013 | Quadri et al. |
| 2013/0144328 A1 | 6/2013 | Weber et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0144382 A1 | 6/2013 | DeStefano |
| 2013/0150954 A1 | 6/2013 | Conklin |
| 2013/0150956 A1 | 6/2013 | Yohanan et al. |
| 2013/0150957 A1 | 6/2013 | Weber |
| 2013/0158600 A1 | 6/2013 | Conklin et al. |
| 2013/0158653 A1 | 6/2013 | Gamarra et al. |
| 2013/0158654 A1 | 6/2013 | Sutton et al. |
| 2013/0158655 A1 | 6/2013 | Sutton et al. |
| 2013/0158656 A1 | 6/2013 | Sutton et al. |
| 2013/0166022 A1 | 6/2013 | Conklin |
| 2013/0166024 A1 | 6/2013 | Drews et al. |
| 2013/0172983 A1 | 7/2013 | Clerc et al. |
| 2013/0178930 A1 | 7/2013 | Straubinger et al. |
| 2013/0183717 A1 | 7/2013 | Marble et al. |
| 2013/0184446 A1 | 7/2013 | Marble et al. |
| 2013/0184811 A1 | 7/2013 | Rowe et al. |
| 2013/0184813 A1 | 7/2013 | Quadri et al. |
| 2013/0184814 A1 | 7/2013 | Huynh et al. |
| 2013/0190861 A1 | 7/2013 | Chau et al. |
| 2013/0190862 A1 | 7/2013 | Pintor et al. |
| 2013/0190865 A1 | 7/2013 | Anderson |
| 2013/0204351 A1 | 8/2013 | Cox et al. |
| 2013/0211504 A1 | 8/2013 | Young |
| 2013/0211508 A1* | 8/2013 | Lane et al. .................... 623/2.11 |
| 2013/0211511 A1 | 8/2013 | Young |
| 2013/0211512 A1 | 8/2013 | Migliazza et al. |
| 2013/0211513 A1 | 8/2013 | Rourke et al. |
| 2013/0231736 A1 | 9/2013 | Essinger et al. |
| 2013/0236889 A1 | 9/2013 | Kishimoto et al. |
| 2013/0238072 A1 | 9/2013 | Deterre et al. |
| 2013/0238073 A1 | 9/2013 | Makdissi et al. |
| 2013/0238087 A1 | 9/2013 | Taylor |
| 2013/0245615 A1 | 9/2013 | Koltz |
| 2013/0245736 A1 | 9/2013 | Alexander et al. |
| 2013/0245750 A1 | 9/2013 | Cunanan et al. |
| 2013/0245751 A1 | 9/2013 | Phung et al. |
| 2013/0253570 A1 | 9/2013 | Bates |
| 2013/0253571 A1 | 9/2013 | Bates |
| 2013/0253635 A1 | 9/2013 | Straubinger et al. |
| 2013/0253637 A1 | 9/2013 | Wang et al. |
| 2013/0253639 A1 | 9/2013 | Alkhatib |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261740 A1 | 10/2013 | Eberhardt et al. |
| 2013/0261742 A1 | 10/2013 | Gaschino et al. |
| 2013/0268064 A1 | 10/2013 | Duffy |
| 2013/0268065 A1 | 10/2013 | Costello et al. |
| 2013/0268068 A1 | 10/2013 | Marchisio et al. |
| 2013/0268069 A1 | 10/2013 | Zakai et al. |
| 2013/0272994 A1 | 10/2013 | Fu et al. |
| 2013/0274606 A1 | 10/2013 | Wei et al. |
| 2013/0274855 A1 | 10/2013 | Stante et al. |
| 2013/0274873 A1 | 10/2013 | Delaloye et al. |
| 2013/0274874 A1 | 10/2013 | Hammer |
| 2013/0281400 A1 | 10/2013 | Yoo et al. |
| 2013/0281420 A1 | 10/2013 | Taraporewala et al. |
| 2013/0281979 A1 | 10/2013 | Arnim et al. |
| 2013/0282028 A1 | 10/2013 | Conklin et al. |
| 2013/0282113 A1 | 10/2013 | Punga et al. |
| 2013/0282114 A1 | 10/2013 | Schweich, Jr. et al. |
| 2013/0289695 A1 | 10/2013 | Tian et al. |
| 2013/0304196 A1 | 11/2013 | Kelly |
| 2013/0304197 A1 | 11/2013 | Buchbinder et al. |
| 2013/0304199 A1 | 11/2013 | Sutton et al. |
| 2013/0304200 A1 | 11/2013 | McLean et al. |
| 2013/0310928 A1 | 11/2013 | Morriss et al. |
| 2013/0310929 A1 | 11/2013 | Dove et al. |
| 2013/0317603 A1 | 11/2013 | McLean et al. |
| 2013/0323302 A1 | 12/2013 | Constable et al. |
| 2013/0324804 A1 | 12/2013 | McKeown et al. |
| 2013/0324815 A1 | 12/2013 | Jian et al. |
| 2013/0325098 A1 | 12/2013 | Desai et al. |
| 2013/0325110 A1 | 12/2013 | Khalil et al. |
| 2013/0325111 A1 | 12/2013 | Campbell et al. |
| 2013/0325114 A1 | 12/2013 | McLean et al. |
| 2013/0325116 A1 | 12/2013 | Sundler et al. |
| 2013/0325117 A1 | 12/2013 | Bruchman et al. |
| 2013/0325121 A1 | 12/2013 | Whatley et al. |
| 2013/0331714 A1 | 12/2013 | Manstrom et al. |
| 2013/0331929 A1 | 12/2013 | Mitra et al. |
| 2013/0331931 A1 | 12/2013 | Gregg et al. |
| 2013/0338698 A1 | 12/2013 | Flanagan |
| 2013/0338763 A1 | 12/2013 | Rowe et al. |
| 2013/0338764 A1 | 12/2013 | Thornton et al. |
| 2013/0338765 A1 | 12/2013 | Braido et al. |
| 2013/0338766 A1 | 12/2013 | Hastings et al. |
| 2013/0345786 A1 | 12/2013 | Behan |

(56) References Cited

U.S. PATENT DOCUMENTS

| | | |
|---|---|---|
| 2013/0345801 A1 | 12/2013 | Conklin et al. |
| 2013/0345803 A1 | 12/2013 | Bergheim, III |
| 2014/0005764 A1 | 1/2014 | Schroeder |
| 2014/0005770 A1 | 1/2014 | Casley et al. |
| 2014/0005772 A1 | 1/2014 | Edelman et al. |
| 2014/0005778 A1 | 1/2014 | Buchbinder et al. |
| 2014/0012373 A1 | 1/2014 | Chau et al. |
| 2014/0014530 A1 | 1/2014 | Lin |
| 2014/0018911 A1 | 1/2014 | Zhou et al. |
| 2014/0018912 A1 | 1/2014 | Delaloye et al. |
| 2014/0018915 A1 | 1/2014 | Biadillah et al. |
| 2014/0025087 A1 | 1/2014 | Richardson |
| 2014/0031857 A1 | 1/2014 | Richardson |
| 2014/0031864 A1 | 1/2014 | Jafari et al. |
| 2014/0031922 A1 | 1/2014 | Duffy et al. |
| 2014/0031923 A1 | 1/2014 | Rogers et al. |
| 2014/0031930 A1 | 1/2014 | Keidar et al. |
| 2014/0039609 A1 | 2/2014 | Campbell et al. |
| 2014/0039611 A1 | 2/2014 | Lane et al. |
| 2014/0039612 A1 | 2/2014 | Dolan |
| 2014/0039614 A1 | 2/2014 | Delaloye et al. |
| 2014/0044689 A1 | 2/2014 | Liu et al. |
| 2014/0044716 A1 | 2/2014 | Paniagua-Solis et al. |
| 2014/0045909 A1 | 2/2014 | Ruby |
| 2014/0046219 A1 | 2/2014 | Sauter et al. |
| 2014/0046353 A1 | 2/2014 | Adams |
| 2014/0046427 A1 | 2/2014 | Michalak |
| 2014/0046433 A1 | 2/2014 | Kovalsky |
| 2014/0046434 A1 | 2/2014 | Rolando et al. |
| 2014/0052170 A1 | 2/2014 | Heuser et al. |
| 2014/0052237 A1 | 2/2014 | Lane et al. |
| 2014/0052238 A1 | 2/2014 | Wang et al. |
| 2014/0052241 A1 | 2/2014 | Harks et al. |
| 2014/0052242 A1 | 2/2014 | Revuelta et al. |
| 2014/0052243 A1 | 2/2014 | Rolando et al. |
| 2014/0052244 A1 | 2/2014 | Rolando et al. |
| 2014/0067048 A1 | 3/2014 | Chau et al. |
| 2014/0067049 A1 | 3/2014 | Costello |
| 2014/0067050 A1 | 3/2014 | Costello et al. |
| 2014/0067052 A1 | 3/2014 | Chau et al. |
| 2014/0067054 A1 | 3/2014 | Chau et al. |
| 2014/0081389 A1 | 3/2014 | Chau et al. |
| 2014/0081391 A1 | 3/2014 | Ruyra-Baliarda et al. |
| 2014/0081393 A1 | 3/2014 | Hasenkam et al. |
| 2014/0086934 A1 | 3/2014 | Shams |
| 2014/0088680 A1 | 3/2014 | Costello et al. |
| 2014/0088685 A1 | 3/2014 | Yevzlin et al. |
| 2014/0088692 A1 | 3/2014 | Wright |
| 2014/0088694 A1 | 3/2014 | Rowe et al. |
| 2014/0088695 A1 | 3/2014 | Figulla et al. |
| 2014/0088696 A1 | 3/2014 | Figulla et al. |
| 2014/0100420 A1 | 4/2014 | Mortier et al. |
| 2014/0100597 A1 | 4/2014 | Wang et al. |
| 2014/0100651 A1 | 4/2014 | Kheradvar et al. |
| 2014/0100653 A1 | 4/2014 | Savage et al. |
| 2014/0107761 A1 | 4/2014 | Gale et al. |
| 2014/0110279 A1 | 4/2014 | Kruetzfeldt et al. |
| 2014/0114340 A1 | 4/2014 | Zhou et al. |
| 2014/0114345 A1 | 4/2014 | Ciobanu et al. |
| 2014/0114391 A1 | 4/2014 | Tabor |
| 2014/0114402 A1 | 4/2014 | Ahlberg et al. |
| 2014/0114408 A1 | 4/2014 | Dwork |
| 2014/0121719 A1 | 5/2014 | Bonner et al. |
| 2014/0121763 A1 | 5/2014 | Duffy et al. |
| 2014/0121764 A1 | 5/2014 | De Paulis et al. |
| 2014/0128726 A1 | 5/2014 | Quill et al. |
| 2014/0128963 A1 | 5/2014 | Quill et al. |
| 2014/0128964 A1 | 5/2014 | Delaloye |
| 2014/0134322 A1 | 5/2014 | Larsen et al. |
| 2014/0135908 A1 | 5/2014 | Glozman et al. |
| 2014/0135909 A1 | 5/2014 | Carr et al. |
| 2014/0142693 A1 | 5/2014 | Krivoruchko et al. |
| 2014/0142694 A1 | 5/2014 | Tabor et al. |
| 2014/0144000 A1 | 5/2014 | Creaven et al. |
| 2014/0148889 A1 | 5/2014 | Deshmukh et al. |
| 2014/0155990 A1 | 6/2014 | Nyuli et al. |
| 2014/0162563 A1 | 6/2014 | Mastrototaro |
| 2014/0163668 A1 | 6/2014 | Rafiee |
| 2014/0172083 A1 | 6/2014 | Bruchman et al. |
| 2014/0172085 A1 | 6/2014 | Quadri et al. |
| 2014/0172086 A1 | 6/2014 | Quadri et al. |
| 2014/0180337 A1 | 6/2014 | Miraki et al. |
| 2014/0186417 A1 | 7/2014 | Trollsas et al. |
| 2014/0188217 A1 | 7/2014 | Rolando et al. |
| 2014/0188219 A1 | 7/2014 | Conklin et al. |
| 2014/0188221 A1 | 7/2014 | Chung et al. |
| 2014/0194975 A1 | 7/2014 | Quill et al. |
| 2014/0194978 A1 | 7/2014 | Seguin et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0200457 A1 | 7/2014 | Shuros et al. |
| 2014/0200649 A1 | 7/2014 | Essinger et al. |
| 2014/0200660 A1 | 7/2014 | Savage et al. |
| 2014/0209238 A1 | 7/2014 | Bonyuet et al. |
| 2014/0213889 A1 | 7/2014 | Macht |
| 2014/0214069 A1 | 7/2014 | Franklin |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214157 A1 | 7/2014 | Börtlein et al. |
| 2014/0214159 A1 | 7/2014 | Vidlund et al. |
| 2014/0214160 A1 | 7/2014 | Naor |
| 2014/0215791 A1 | 8/2014 | Soundararajan et al. |
| 2014/0221823 A1 | 8/2014 | Keogh et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0228945 A1 | 8/2014 | Valdez et al. |
| 2014/0230515 A1 | 8/2014 | Tuval et al. |
| 2014/0236287 A1 | 8/2014 | Clague et al. |
| 2014/0236288 A1 | 8/2014 | Lambrecht et al. |
| 2014/0243692 A1 | 8/2014 | Baumann et al. |
| 2014/0243879 A1 | 8/2014 | Rothstein et al. |
| 2014/0243880 A1 | 8/2014 | Schotzko et al. |
| 2014/0243953 A1 | 8/2014 | Stante et al. |
| 2014/0256035 A1 | 9/2014 | Strasly et al. |
| 2014/0257463 A1 | 9/2014 | Sweeney et al. |
| 2014/0257467 A1 | 9/2014 | Lane et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277403 A1 | 9/2014 | Peter |
| 2014/0277408 A1 | 9/2014 | Folan |
| 2014/0277409 A1 | 9/2014 | Börtlein et al. |
| 2014/0277410 A1 | 9/2014 | Börtlein et al. |
| 2014/0277411 A1 | 9/2014 | Börtlein et al. |
| 2014/0277412 A1 | 9/2014 | Börtlein et al. |
| 2014/0277418 A1 | 9/2014 | Miller |
| 2014/0277419 A1 | 9/2014 | Garde et al. |
| 2014/0277423 A1 | 9/2014 | Alkhatib et al. |
| 2014/0277427 A1 | 9/2014 | Ratz et al. |
| 2014/0288480 A1 | 9/2014 | Zimmerman et al. |
| 2014/0296973 A1 | 10/2014 | Bergheim et al. |
| 2014/0296975 A1 | 10/2014 | Tegels et al. |
| 2014/0303667 A1 | 10/2014 | Cox et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330366 A1 | 11/2014 | Dehdashtian et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1 | 11/2014 | Duffy et al. |
| 2014/0336720 A1 | 11/2014 | Casset et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350523 A1 | 11/2014 | Dehdashtian et al. |

(56) References Cited

U.S. PATENT DOCUMENTS

| | | |
|---|---|---|
| 2014/0350666 A1 | 11/2014 | Righini |
| 2014/0350668 A1 | 11/2014 | Delaloye et al. |
| 2014/0356519 A1 | 12/2014 | Hossainy et al. |
| 2014/0358221 A1 | 12/2014 | Ho et al. |
| 2014/0358223 A1 | 12/2014 | Rafiee et al. |
| 2014/0364404 A1 | 12/2014 | Cleek et al. |
| 2014/0364939 A1 | 12/2014 | Deshmukh et al. |
| 2014/0364943 A1 | 12/2014 | Conklin |
| 2014/0364944 A1 | 12/2014 | Lutter et al. |
| 2014/0370071 A1 | 12/2014 | Chen et al. |
| 2014/0370599 A1 | 12/2014 | Strasly et al. |
| 2014/0371833 A1 | 12/2014 | Ghosh et al. |
| 2014/0371841 A1 | 12/2014 | Casley et al. |
| 2014/0371842 A1 | 12/2014 | Marquez et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0373334 A1 | 12/2014 | Gamarra et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2014/0379095 A1 | 12/2014 | Waisblatt et al. |
| 2015/0005873 A1 | 1/2015 | Chang et al. |
| 2015/0007630 A1 | 1/2015 | Maimon et al. |
| 2015/0012085 A1 | 1/2015 | Salahieh et al. |
| 2015/0018625 A1 | 1/2015 | Miraki et al. |
| 2015/0018879 A1 | 1/2015 | Moehle et al. |
| 2015/0018938 A1 | 1/2015 | Von Segesser et al. |
| 2015/0018939 A1 | 1/2015 | Colson et al. |
| 2015/0018944 A1 | 1/2015 | O'Connell et al. |
| 2015/0025621 A1 | 1/2015 | Costello et al. |
| 2015/0025622 A1 | 1/2015 | Creaven et al. |
| 2015/0025623 A1 | 1/2015 | Granada et al. |
| 2015/0025624 A1 | 1/2015 | Dwork et al. |
| 2015/0026635 A1 | 1/2015 | Gohr et al. |
| 2015/0032153 A1 | 1/2015 | Quadri |
| 2015/0032174 A1 | 1/2015 | Ghosh |
| 2015/0039081 A1 | 2/2015 | Costello |
| 2015/0051698 A1 | 2/2015 | Ruyra Baliarda et al. |
| 2015/0066137 A1 | 3/2015 | Chen et al. |
| 2015/0066140 A1 | 3/2015 | Quadri |
| 2015/0073537 A1 | 3/2015 | Jimenez et al. |
| 2015/0081009 A1 | 3/2015 | Quadri |
| 2015/0081011 A1 | 3/2015 | Young et al. |
| 2015/0086603 A1 | 3/2015 | Hossainy et al. |
| 2015/0088245 A1 | 3/2015 | Costello |
| 2015/0088250 A1 | 3/2015 | Zeng et al. |
| 2015/0088252 A1 | 3/2015 | Jenson et al. |
| 2015/0094803 A1 | 4/2015 | Navia |
| 2015/0100118 A1 | 4/2015 | Benton |
| 2015/0105847 A1 | 4/2015 | Ollivier et al. |
| 2015/0105856 A1 | 4/2015 | Rowe et al. |
| 2015/0112430 A1 | 4/2015 | Creaven et al. |
| 2015/0119692 A1 | 4/2015 | McHenry et al. |
| 2015/0119974 A1 | 4/2015 | Rothstein et al. |
| 2015/0119980 A1 | 4/2015 | Beith et al. |
| 2015/0119982 A1 | 4/2015 | Quill et al. |
| 2015/0122687 A1 | 5/2015 | Zeng et al. |
| 2015/0127093 A1 | 5/2015 | Hosmer |
| 2015/0148731 A1 | 5/2015 | McNamara et al. |
| 2015/0157458 A1 | 6/2015 | Thambar et al. |
| 2015/0196390 A1 | 7/2015 | Ma et al. |
| 2015/0196393 A1 | 7/2015 | Vidlund |
| 2015/0209137 A1 | 7/2015 | Quadri |
| 2015/0238315 A1 | 8/2015 | Rabito et al. |

FOREIGN PATENT DOCUMENTS

| | | |
|---|---|---|
| DE | 3128704 | 2/1983 |
| DE | 10 2006 052 564 | 12/2007 |
| EP | 0 657 147 | 6/1995 |
| EP | 1 472 996 B1 | 11/2004 |
| EP | 1 255 510 B1 | 4/2007 |
| GB | 1264471 | 2/1972 |
| GB | 1315 844 | 5/1973 |
| GB | 2245495 | 1/1992 |
| GB | 2 398 245 | 8/2004 |
| JP | 2002-540889 | 12/2002 |
| JP | 2008-541865 | 11/2008 |
| WO | WO 97/49355 | 12/1997 |
| WO | WO 00/53104 | 9/2000 |
| WO | WO 00/61034 | 10/2000 |
| WO | WO 01/35861 | 5/2001 |
| WO | WO 01/35870 | 5/2001 |
| WO | WO 01/72239 | 10/2001 |
| WO | WO 02/036048 | 5/2002 |
| WO | WO 03/032554 | 11/2003 |
| WO | WO 03/028522 | 1/2004 |
| WO | WO 2004/014257 | 2/2004 |
| WO | WO 2004/014474 | 2/2004 |
| WO | WO 2004/058097 | 7/2004 |
| WO | WO 2005/002466 | 1/2005 |
| WO | WO 2005/011534 | 2/2005 |
| WO | WO 2005/041810 | 5/2005 |
| WO | WO 2005/087140 | 9/2005 |
| WO | WO 2006/070372 | 7/2006 |
| WO | WO 2006/085304 | 8/2006 |
| WO | WO 2006/089236 | 8/2006 |
| WO | WO 2006/127765 | 11/2006 |
| WO | WO 2007/025028 | 3/2007 |
| WO | WO 2007/034488 | 3/2007 |
| WO | WO 2007/058847 | 5/2007 |
| WO | WO 2007/058857 | 5/2007 |
| WO | WO 2007/103229 | 9/2007 |
| WO | WO 2007/123658 | 11/2007 |
| WO | WO 2007/134290 | 11/2007 |
| WO | WO 2008/005535 | 1/2008 |
| WO | WO 2008/013915 | 1/2008 |
| WO | WO 2008/035337 | 3/2008 |
| WO | WO 2008/070797 | 6/2008 |
| WO | WO 2008/091515 | 7/2008 |
| WO | WO 2008/103722 | 8/2008 |
| WO | WO 2008/150529 | 12/2008 |
| WO | WO 2009/026563 | 2/2009 |
| WO | WO 2009/033469 | 3/2009 |
| WO | WO 2009/045331 | 4/2009 |
| WO | WO 2009/053497 | 4/2009 |
| WO | WO 2009/091509 | 7/2009 |
| WO | WO 2009/094500 | 7/2009 |
| WO | WO 2009/108355 | 9/2009 |
| WO | WO 2009/134701 | 11/2009 |
| WO | WO 2009/137359 | 11/2009 |
| WO | WO 2009/155561 | 12/2009 |
| WO | WO 2010/008549 | 1/2010 |
| WO | WO 2010/037141 | 4/2010 |
| WO | WO 2010/040009 | 4/2010 |
| WO | WO 2010/042950 | 4/2010 |
| WO | WO 2010/057262 | 5/2010 |
| WO | WO 2010/098857 | 9/2010 |
| WO | WO 2011/025945 | 3/2011 |
| WO | WO 2011/081997 | 7/2011 |
| WO | WO 2011/137531 | 11/2011 |
| WO | WO 2012/035279 | 3/2012 |
| WO | WO 2012/095455 | 7/2012 |
| WO | WO 2012/177942 | 12/2012 |
| WO | WO 2013/028387 | 2/2013 |
| WO | WO 2013/059747 | 4/2013 |
| WO | WO 2014/021905 | 2/2014 |
| WO | WO 2014/022124 | 2/2014 |

OTHER PUBLICATIONS

US 8,221,315, 07/2012, Lambrecht et al. (withdrawn)
U.S. Appl. No. 14/186,989, filed Feb. 21, 2014, Quadri et al.
U.S. Appl. No. 14/197,590, filed Mar. 5, 2014, Ratz et al.
U.S. Appl. No. 14/197,690, filed Mar. 5, 2014, Ratz et al.
CardiAQ Valve Technologies, "Innovations in Heart Valve Therapy," In3 San Francisco, Jun. 18, 2008, PowerPoint presentation in 19 slides.
European Extended Search Report, re EP Application No. 14159378.0, dated Jul. 24, 2014.
Neovasc Surgical Products, "Neovasc Surgical Products: An Operating Division of Neovasc Inc.," dated Apr. 2009.

(56) References Cited

OTHER PUBLICATIONS

Kronemyer, Bob: "CardiAQ Valve Technologies: Percutaneous Mitral Valve Replacement," Start Up—Windhover Review of Emerging Medical Ventures, vol. 14, No. 6, Jun. 2009, pp. 48-49.
Bavaria, Joseph E. M.D.: "CardiAQ Valve Technologies: Transcatheter Mitral Valve Implantation," Sep. 21, 2009.
Ostrovsky, Gene: "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
European Extended Search Report, re EP Application No. 14159090.1, dated Jul. 22, 2014.
U.S. Appl. No. 14/598,568, filed Jan. 16, 2015, Quadri et al.
U.S. Appl. No. 14/628,034, filed Feb. 20, 2015, Rabito et al.
U.S. Appl. No. 14/702,233, filed May 1, 2015, Arshad et al.
U.S. Appl. No. 14/716,507, filed May 19, 2015, Ratz et al.
U.S. Appl. No. 14/724,355, filed May 28, 2015, Rabito et al.
Grube et al,: "Percutaneous Implantation of the CoreValve Self-Expanding Valve Prosthesis in High-Risk Patients With Aortic Valve Disease," Valvular Heart Disease, circ.ahajournals.org (2006; 114:1616-1624) Published on line before print Oct. 2, 2006.
Businesswire.com, "50 Early-to Late-Stage Medical Device Companies Seeking Investment and Partnering Opportunities to Present in 3 Weeks at 'Investment in Innovation (In3) Medical Device Summit,'" May 27, 2008.
Ratz, J. Brent, "LSI EMT Spotlight," May 15, 2009.
"CVT's Transcatheter Mitral Valve Implantation (TMVI) platform might be the 'next big thing' in the cardiac cath lab," Jun. 2, 2009.
Ratz, J. Brent, "In3 Company Overview," Jun. 24, 2009.
"Company Overview" Jun. 25, 2009 at TVT.
"CVT is developing a non-surgical approach to replacing mitral valves that may be the alternative to open-chest surgery," believed to be published in Sep. 2009.
Enhancedonlinenews.com, "CardiAQ Valve Technologies (CVT) Discloses Successful Results of Acute In Vivo Study of Its Novel Transcatheter Mitral Valve Implantation (TMVI) System," Sep. 28, 2009.
Wayback Machine, "http://www.cardiaq.com/" indicated as archived on Jan. 16, 2010.
Wayback Machine, "http://www.cardiaq.com/technology.html" indicated as archived on Jan. 17, 2010.
"Surveying the Landscape," unknown publication date.
Banai, Shmuel, et al., Tiara: A Novel Catheter-Based Mitral Valve Bioprosthesis, Initial Experiments and Short-Term Pre-Clinical Results, Journal of the American College of Cardiology, vol. 60, No. 15, 2012. Applicant believes that this may have been available online as early as Sep. 12, 2012.
Banai et al.: "Transapical Mitral Implantation of the Tiara Bioprosthesis," JACC: Cardiovascular Interventions, vol. 7, No. 2, Feb. 2014:154-62.
Bavaria, Joseph E. M.D. et al.: "Transcatheter Mitral Valve Implantation: the Future Gold Standard for MR?," Applicant requests the Examiner to consider this reference to be prior art as of Dec. of 2010.
Berreklouw, Eric, MD, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 4, 2011.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Boudjemline, Younes, MD, et al., "Steps Toward the Percutaneous Replacement of Atrioventricular Valves," JACC, vol. 46, No. 2, Jul. 19, 2005:360-5.

Brinkman, William T., MD, et al., Transcatheter Cardiac Valve Interventions, Surg Clin N Am 89 (2009) 951-966, Applicant believes this may have been available as early as Aug. of 2009.
Businesswire.com, "CardiAQ Valve Technologies (CVT) Discloses Successful Results of Acute In Vivo Study of Its Novel Transcatheter Mitral Valve Implantation (TMVI) System," Sep. 28, 2009.
Businesswire.com, CardiAQ Valve Technologies, "CardiAQ Valve Technologies ("CVT") to disclose data during 'EuroPCR 2010' about the world's first successful in vivo transcatheter delivery of a mitral heart valve implant," Irvine, California, May 20, 2010.
CardiAQ Valve Technologies Company Fact Sheet 2009.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. of 2006.
Diagnostic and Interventional Cardiology, "Neovasc Announces Publication of Tiara Transcatheter Mitral Valve Preclinical Data in JACC," Sep. 18, 2012, p. 1, http://www.dicardiology.com/content/neovasc-announces-publication-tiara-transcatheter-mitral-valve-preclinical-data-jacc.
Diagnostic and Interventional Cardiology, "Neovasc Announces Successful Human Implant of Tiara Transcatheter Mitral Valve," Feb. 18, 2014, p. 1, <http://www.dicardiology.com/article/neovasc-announces-successful-human-implant-tiara-transcatheter-mitral-valve>.
Diagnostic and Interventional Cardiology, "Neovasc Receives First U.S. Patent for its Tiara Transcatheter Mitral Valve Replacement Technology," Nov. 15, 2013, p. 1, <http://www.dicardiology.com/content/neovasc-receives-first-us-patent-its-tiara-transcatheter-mitral-valve-replacement-technology>.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Aug. 20, 2013.
Feldman, Ted, MD. "Prospects for Percutaneous Valve Therapies," Circulation 2007;116:2866-2877. Applicant believes that this may be available as early as Dec. 11, 2007.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Gillespie, Matthew J., MD, et al., "Sutureless Mitral Valve Replacement: Initial Steps Toward a Percutaneous Procedure," Ann Thorac Surg. Aug. 2013; 96(2).
Grewal, Jasmine, et al, "Mitral Annular Dynamics in Myxomatous Valve Disease: New Insights With Real-Time 3-Dimensional Echocardiography," Circ. Mar. 30, 2010.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Wayback Machine, Neovasc Ostial Products Overview, https://web.archive.org/web/20090930050359/https://www.neovasc.com/vascular-products/ostialproducts/default.php, indicated as archived on Sep. 30, 2008.
JenaValve Technology, "The JenaValve—The Prosthesis", 2011 JenaValve Technology in 1 page.

(56) References Cited

OTHER PUBLICATIONS

Karimi, Houshang, MD, et al., "Percutaneous Valve Therapies," SIS 2007 Yearbook, Chapter 11, pp. 1-11.
Lansac, et al., "Dynamic balance of the aortomitral junction," J. Thoracic & Cardiovascular Surgery, 123(5):911-918 (2002).
Lauten, Alexander, et al., "Experimental Evaluation of the JenaClip Transcatheter Aortic Valve," Catheterization and Cardiovascular Interventions 74:514-519, published online May 11, 2009, Applicant believes this may have been available online as early as Apr. 27, 2009.
Leon, Martin B., MD, et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lozonschi, Lucian, MD, et al., "Transapical Mitral Valved Stent Implantation," Ann Thorac Surg 2008;86:745-8 in 4 pages, Applicant believes this may have been available as early as Sep. of 2008.
Lutter, Georg, et al., "Off-Pump Transpaical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents For Off-Pump Mitral Valve Replacement," European Journal of Cardio-thoracic Surgery 28 (2005) 194-199, Applicant believes this may have been available as early as Aug. of 2005.
Mack, Michael M.D., "Advantages and Limitations of Surgical Mitral Valve Replacement; Lessons for the Transcatheter Approach," Applicant believes this may have been available.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on Nov. of 2011 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Neovasc corporate presentation, Oct. 2009, available at http://www.neovasc.com/investors/documents/Neovasc-Corporate-Presentation-October-2009.pdf.
Ormiston, et al., "Size and Motion Of The Mitral Valve Annulus In Man. I. A Two-Dimensional Echocardiographic Method and Findings In Normal Subjects," Circulation, 64(1):113-120 (1981).
Ostrovsky, Gene, "A Trial of Zenith Fenestrated AAA Endovascular Graft Goes On," medGadget, Aug. 1, 2008, available at: :http://www.medgadget.com/2008/08/a_trial_of_zenith_fenestrated_aaa_endovascular_graft_goes_on.html.
Otto, C, "Evaluation and Management of Chronic Mitral Regurgitation," New Engl. J. Med., 354:740-746 (2001). Published Sep. 6, 2001.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. of 2008.
Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent et al., "Fabric, Skin, Cloth expansion . . . best approach'?," AREA by Autodesk, 3ds Max: Modeling, Forum postings from Feb. 18, 2009 to Feb. 19, 2009, http://area.autodesk.com.
Ratz, J. Brent et al., "Isolating Interpolation," Arch-Pub.com, Architecture Forums: Animation and Rigging, Forum postings from Feb. 9, 2009 to Feb. 10, 2009, http://www.arch-pub.com.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at EuroPCR May 2013.
Sondergaard, Lars, et al., "Transcatheter Mitral Valve Implantation: CardiAQ™," Applicant believes this may have been presented at TCT Oct. 2013.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
"Update," Applicant believes this may have been presented on Jun. 6, 2010 at TVT.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Vu, Duc-Thang, MD, et al., "Novel Sutureless Mitral Valve Implantation Method Involving a Bayonet Insertion and Release Mechanism: A Proof Of Concept Study In Pigs," The Journal of Thoracic and Cardiovascular Surgery, vol. 143, No. 4, 985-988, Apr. 2012, Applicant believes this may have been available online as early as Feb. 11, 2012.
Walther, Thomas et al., "Transapical Approach for Sutureless Stent-Fixed Aortic Valve Implantation: Experimental Results," European Journal of Cardio-thoracic Surgery 29 (2006) 703-708, Applicant believes this may have been available as early as May of 2006.
Webb, John G., et al., "Transcatheter Aortic Valve Implantation: The Evolution Of Prostheses, Delivery Systems And Approaches," Archives of Cardiovascular Disease (2012) 105, 153-159, Applicant believes this may have been available as early as Mar. 16, 2012.
Yamada, et al., "The Left Ventricular Ostium: An Anatomic Concept Relevant to Idiopathic Ventricular Arrhythmias", Circ. Arrhythmia Electrophysiol., 1:396-404 (Dec. 2008).
U.S. Appl. No. 61/169,367, filed Apr. 15, 2009, Quadri.
U.S. Appl. No. 29/484,001, filed Mar. 5, 2014, Pesce et al.

\* cited by examiner

PROSTHESIS WITH OUTER SKIRT AND ANCHORS

CROSS-REFERENCE TO RELATED APPLICATIONS

This application claims the benefit of priority to U.S. Provisional Appl. Nos. 61/782,707, filed Mar. 14, 2013 and 61/789,783, filed Mar. 15, 2013. The entire contents of the above applications are hereby incorporated by reference and made a part of this specification. Any and all priority claims identified in the Application Data Sheet, or any correction thereto, are hereby incorporated by reference under 37 CFR 1.57.

BACKGROUND OF THE INVENTION

1. Field of the Invention

Certain embodiments disclosed herein relate generally to prostheses for implantation within a lumen or body cavity. In particular, certain embodiments relate to expandable prostheses such as replacement heart valves, such as for the mitral valve, that are configured to atraumatically grasp intralumenal tissue.

2. Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage has proven particularly challenging. An additional challenge relates to the ability of such prostheses to be secured relative to intralumenal tissue, e.g., tissue within any body lumen or cavity, in an atraumatic manner. Further challenges arise when trying to controllably deliver and secure such prostheses in a location such as at a native mitral valve.

SUMMARY OF THE INVENTION

Embodiments of the present disclosure are directed to a prosthesis, such as but not limited to a replacement heart valve. According to some embodiments, a prosthesis can be configured to be deployed within a body cavity and prevent axial flow of fluid around an exterior of the prosthesis. The prosthesis can include an expandable frame configured to radially expand and contract for deployment within the body cavity, and an outer skirt positioned annularly around an exterior of the expandable frame. In some embodiments, the outer skirt can extend outward from the frame and be secured to an outwardly extending anchor on the frame to create an axial barrier to fluid flow exterior to the frame when deployed within the body cavity. Further embodiments are directed to methods of delivering a prosthesis, e.g. a replacement heart valve, and methods of using a prosthesis to create a barrier to fluid flow exterior to the prosthesis (e.g., to prevent paravalvular leakage).

In some embodiments a prosthesis can be configured to grasp intralumenal tissue when deployed within a body cavity and prevent axial flow of fluid around an exterior of the prosthesis. The prosthesis can comprise an expandable frame, a plurality of proximal anchors, a plurality of distal anchors, and a skirt. The expandable frame can comprise a proximal end and a distal end and a longitudinal axis extending therethrough, the frame configured to radially expand and contract for deployment within the body cavity. The plurality of proximal anchors can each connect to the frame so that when the frame is in an expanded configuration an end of each proximal anchor is positioned radially outward from the frame and extends generally distally. The plurality of distal anchors can each connect to the frame so that when the frame is in an expanded configuration an end of each distal anchor is positioned radially outward from the frame and extends generally proximally, wherein the ends of the distal anchors are axially spaced from the ends of the proximal anchors when the frame is in an expanded configuration. The skirt can be annularly positioned around an exterior of the expandable frame and secured to at least some of the plurality of proximal anchors to create an axial barrier to fluid flow exterior to the frame when deployed within the body cavity. In some embodiments, the frame can be configured such that radial expansion of the frame causes the ends of the plurality of proximal anchors and the ends of the plurality of distal anchors to draw closer together.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION OF THE PREFERRED EMBODIMENTS

The present specification and drawings provide aspects and features of the disclosure in the context of several embodiments of prostheses, replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within a vein, or the like. In addition, particular features of a valve, delivery device, etc. should not be taken as limiting, and features of any one embodiment discussed herein can be combined with features of other embodiments as desired and when appropriate.

Figure 1A:
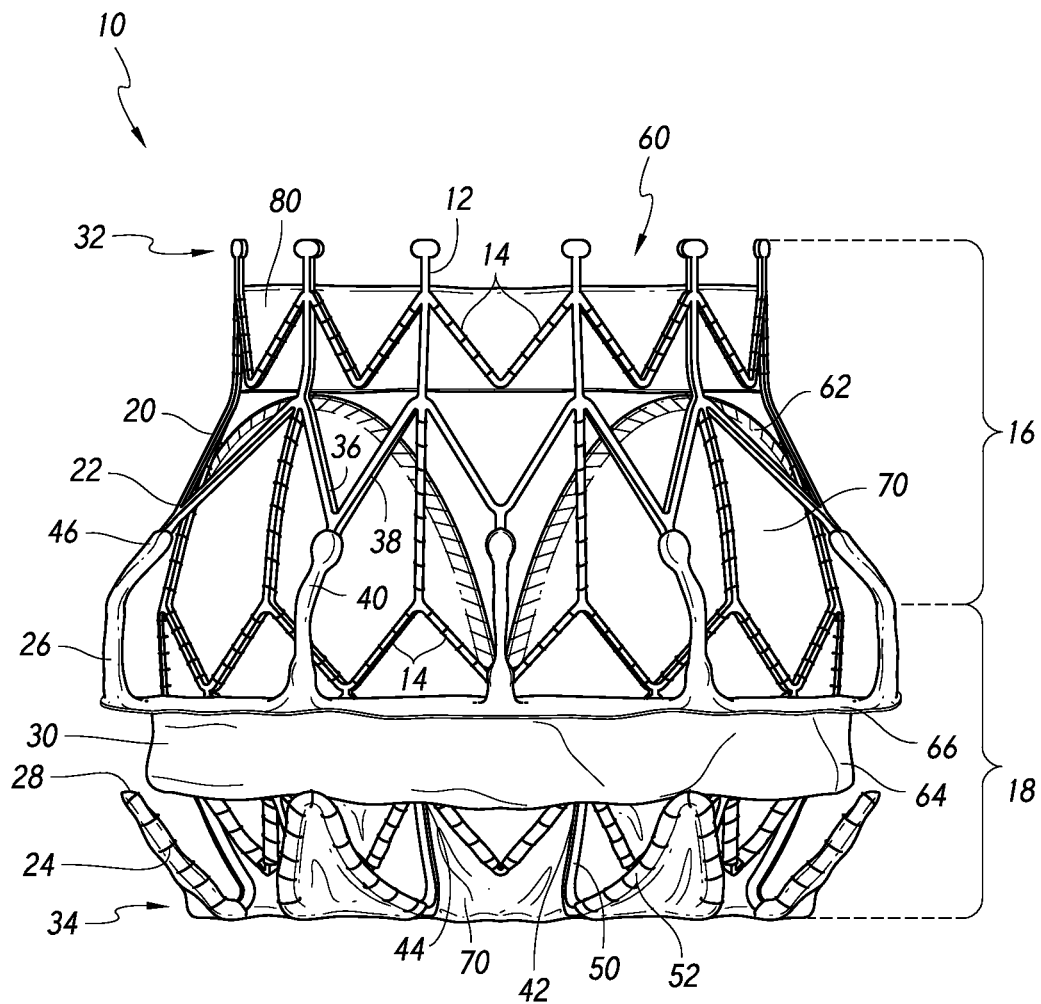
FIG. 1A is a side view of an embodiment of a prosthesis configured as a replacement heart valve.
Figure 1B:
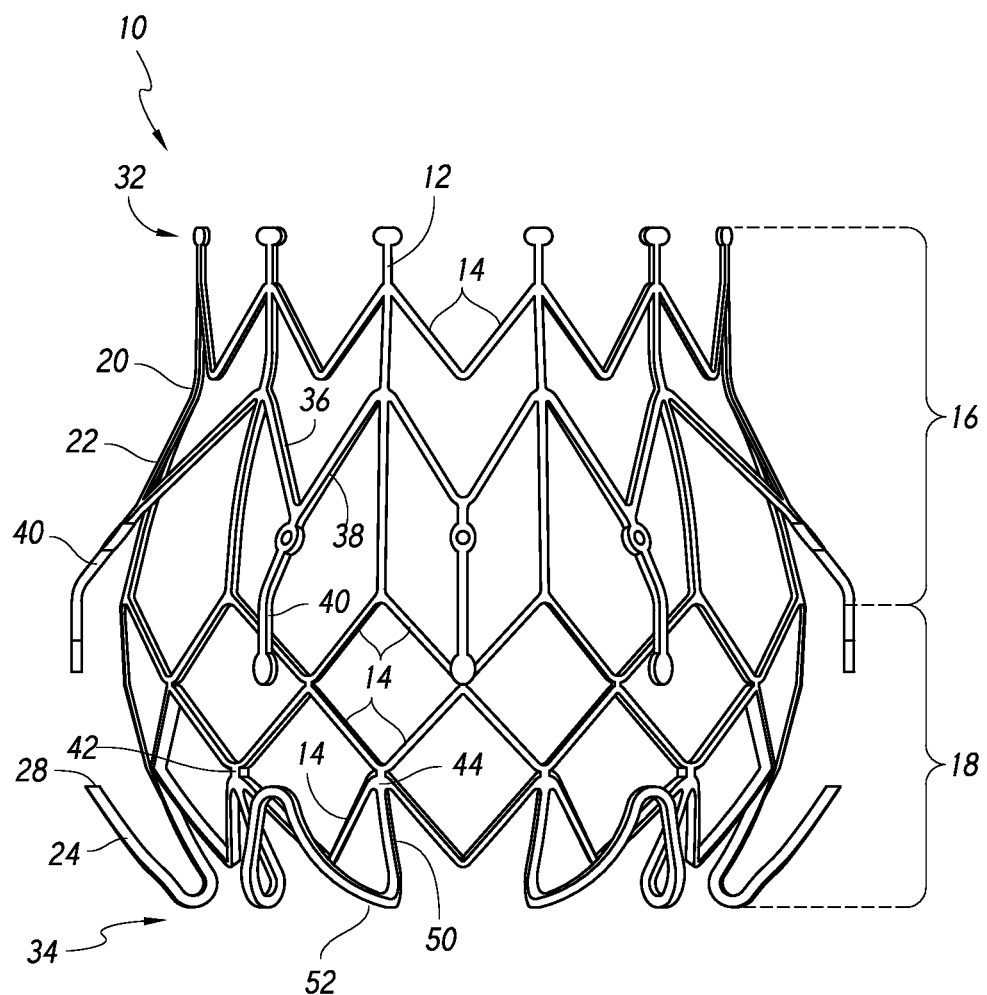
FIG. 1B is a side view of the frame from the prosthesis of FIG. 1A.

With initial reference to FIGS. 1A-B, an embodiment of a prosthesis 10 is shown. The illustrated prosthesis 10 includes a frame 20 that may be self-expanding or balloon expandable. The frame 20 (as best seen in FIG. 1B) can include a proximal end 32, a distal end 34 and proximal 22 and distal 24 anchors. The anchors can allow the frame to engage a native valve annulus or other tissue to be implanted at a target location. The prosthesis 10 can include one or more of a valve 60, an outer skirt 30, a valve skirt 70 and a support band 80. The valve 60 can be designed to replace a damaged or diseased native heart valve such as a mitral valve; though it will be understood that a replacement valve is not required as part of the prosthesis.

The prosthesis can be a replacement heart valve similar to that and including features similar to those disclosed in U.S. Provisional Appl. No. 61/782,707, filed Mar. 14, 2013, U.S. Pat. No. 8,403,983 and U.S. Publication Nos. 2010/0298931, 2011/0313515 and 2012/0078353 the entireties of each of which are hereby incorporated by reference and made a part of this specification. This is inclusive of the entire disclosure and is not in any way limited to the disclosure of the replacement heart valve.

The frame 20 can be made of many different materials, but is preferably made from metal. In some embodiments, the frame 20 can be made from a shape memory material, such as nitinol. A wire frame or a metal tube can be used to make the frame. The wire frame of a metal tube can be cut or etched to remove all but the desired metal skeleton. In some embodiments a metal tube is laser cut in a repeating pattern to form the frame. The flat pattern can be cut from a metal tube and then the tube can be bent and expanded to the shape shown in FIGS. 1A-B. The frame 20 can further be expanded and/or compressed and/or otherwise worked to have the desired shape or shapes, such as for introduction and implantation.

As shown, the frame when in an expanded configuration, such as in a fully expanded configuration, has a bulbous or slightly bulbous shape, with a middle portion being larger than the proximal 32 and distal 34 ends. In some embodiments, the inside diameter of the both ends can be the same, or it can be bigger on one end than the other, while still having a middle portion larger than both the proximal and distal ends. In some embodiments, the effective diameter of the distal frame end is smaller than the effective diameter of the middle portion. The bulbous shape of the frame can advantageously allow the frame to engage a native valve annulus or other body cavity, while spacing the inlet and outlet from the heart or vessel wall. This can help reduce undesired contact between the prosthesis and the heart or vessel, such as the ventricular wall of the heart. In other embodiments, the frame may not have a bulbous portion, and can have substantially the same outer dimension along its entire length, or it may have one end larger than the other end. The prosthesis 10 and frame 20 may be similar to the replacement heart valves and associated frames, and may incorporate and/or interchange features disclosed in U.S. Provisional Appl. No. 61/782,707, U.S. Pat. No. 8,403,983 and U.S. Publication Nos. 2010/0298931 and 2011/0313515, the entireties of each of which are hereby incorporated by reference and made a part of this specification. This is inclusive of the entire disclosure and is not in any way limited to the disclosure of the replacement heart valves and associated frames.

A number of struts collectively make up the frame 20. FIGS. 1A-B illustrate the frame in an expanded configuration with a number of longitudinal struts 12 and undulating struts 14, with cells defined by the open spaces between the struts. The longitudinal struts may be arranged so that they are parallel or generally or substantially parallel to a longitudinal axis of the frame. The longitudinal axis of the frame may be defined as the central axis that extends through the center of the frame between the proximal 32 and distal 34 ends. Any number of configurations of struts can be used, such as the rings of undulating struts shown forming chevrons and diamonds, but also ovals, curves, and various other shapes. The illustrated embodiment includes two rings, or rows of chevrons shown in portion 16 and two rows of diamond-shaped cells shown in portion 18. The two rows of diamonds are partially obscured by the outer skirt 30.

The frame 20 has a non-foreshortening portion 16 and a foreshortening portion 18. These portions can be defined by the frame 20 and the positioning of various types of struts along the frame 20. In the figures it can be seen that the longitudinal struts 12 span the length of the non-foreshortening portion 16, while undulating struts 14 form the foreshortening portion 18. When the frame is radially collapsed or compacted, the struts 14 become more parallel with respect to the longitudinal axis of the frame, causing an outer diameter of the frame to decrease and the longitudinal length of the frame to increase in the foreshortening portion 18. As the frame moves from a compacted position to an expanded position, the longitudinal length of the frame can decrease in the foreshortening portion 18. But, the frame length does not substantially change length in the non-foreshortening portion 16.

Foreshortening of the frame 20 can be used to engage and secure the prosthesis to intralumenal tissue in a body cavity, for example tissue at or adjacent a native valve, such as a native valve annulus and/or leaflets. Opposing anchors 22, 24 can be constructed on the frame 20 so that portions of the anchors, such as tips or ends 26, 28, move closer together as the frame foreshortens. As one example, this can allow the anchors 22, 24 to grasp tissue on opposite sides of the native mitral annulus to thereby secure the prosthesis at the mitral valve.

The anchors 22, 24 and anchor tips 26, 28 can be located anywhere along the frame 20 just so long as at least one of the anchors is either connected to the foreshortening portion 18 or the foreshortening portion is positioned between the anchors so that a portion of the anchors will be move closer together with expansion of the frame. As shown, the anchors 24 are connected to the foreshortening portion 18. The foreshortening portion can also be positioned anywhere along the frame, though it is shown towards the distal end 34. In some embodiments, both of the anchor tips 26, 28 are located in the foreshortening portion 18. In some embodiments, the foreshortening portion 18 may extend the entire length of the frame, such that there is no non-foreshortening portion 16.

Preferably, each of the anchors 22, 24 is positioned or extends generally radially outwardly from the frame 20 so that the anchor tips 26, 28 are generally spaced away or radially outward from the rest of the frame 20. For example, the anchor tips may be located radially outward from the middle portion of the frame, with the tips 26 and 28 being axially spaced from one another. In some embodiments, all or part of the structure connected to the anchor tip and extending radially from the frame, including one or more rings and/or struts, can be considered part of the anchor. The anchors can include a base located on the anchor on a side opposite the tip. The base can be for example where the anchor begins to extend from or away from the frame 20.

For example, proximal anchors 22 are shown having first 36 and second 38 struts forming a chevron and connected to longitudinal struts 12 at a base of the anchor. The first and second struts of the anchor 22 are bent at the base so that the anchor 22 extends radially outwardly from the frame as it extends generally distally towards the tip 26. The first and second struts can be connected to each other at a radially outward location to form an outwardly extending loop, and in some embodiments, the first and second struts can be joined at a third strut 40 that continues to extend outwardly and/or generally distally and is then bent such that the tip points distally and extends in a manner generally parallel with the longitudinal axis of the prosthesis. The anchor also includes an eyelet 46. As illustrated, the eyelet is located along the third strut 40, though the eyelet can be positioned in other locations along the anchor 22, such as at the distal end. The tips 26 of the proximal anchors may extend distally and be parallel or substantially parallel with the longitudinal axis of the frame, or the tips 26 may extend generally distally but still radially outwardly inclined or at an acute angle relative to the longitudinal axis of the frame.

As another example, the distal anchors 24 are shown having looped anchors. Each looped anchor has a first base 42 and a second base 44 connected to the frame, wherein the first and second bases are at opposite corners of the same cell. Alternatively, the first and second bases may be located at the distal most corners of adjacent cells. The distal anchors 24 extends generally distally from the frame at the first base 42 but then is bent back around and begins to extend outwardly from the frame in a generally proximal direction. The distal anchor 24 then repeats this configuration in reverse towards the second base 44 such that the two sides of the looped anchor are mirror images of one another. It will be understood that the looped anchor can have other configurations and that it may not be symmetrical.

As illustrated in FIGS. 1A-B, the tips 28 of the distal anchors are circumferentially aligned with the tips 26 of the proximal anchors, though in other embodiments, the tips 28 of the distal anchors may be circumferentially staggered between the tips 26 of the proximal anchors. In the embodiment of FIGS. 1A-B, adjacent distal anchors 26 are spaced apart by one cell, though in other embodiments, adjacent distal anchors may be provided on adjacent cells. Thus, for example, instead of having six distal anchors and twelve proximal anchors as shown in FIGS. 1A-B, there may be a 1:1 correspondence between proximal and distal anchors.

The distal anchors 24 can be positioned to be not as far radially outward as the proximal anchors, and the tips 28 may be positioned radially inward of the tips 26. As described further below, such a configuration may be advantageous in positioning and securing the prosthesis in a mitral valve or other body location. As shown, the distal anchors 24 may comprise loops as described above, having a curved or arcuate atraumatic tip to minimize damage to body tissue.

The illustrated looped distal anchor is made up of the following segments. The first segment 50 extends generally longitudinally with the frame, extending distally or generally distally (e.g., slightly radially inward) with the frame. The strut is then bent back around to point in generally the opposite direction at the second segment 52. The second segment 52 ends in the rounded tip 28 and then the anchor strut repeats to form the mirror image. After the second segment 52 bends back around to point in generally the opposite direction, in the embodiment illustrated the second segment may first extend radially outward at an acute angle relative to the longitudinal axis before bending into a portion that extends parallel or substantially parallel to the longitudinal axis. The paired second segments 52 may extend parallel or generally parallel with one another at least near the tip, though they may also move slightly towards or away from each other in some embodiments. The distal anchors 24 can positioned outward from the frame and yet inward from the position of the proximal anchors 22.

It will be understood that the anchors can have various other configurations. In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either distally or proximally before and/or after one or more of the bending stages. A portion of the anchor may extend with the frame before or after any bending stages.

In the illustrated embodiment there are twelve proximal anchors 22 and six distal anchors 24. It will be understood that other numbers and groupings of anchors can be used. For example, in some embodiments with twelve distal anchors, two anchors can share the first segment 50 where the anchor base 42, 44 is connected to the frame. In some embodiments there may be twelve anchors on one side and twelve on the other. In addition, the distal and proximal anchors may be aligned so the tips point generally towards each other, or they may be spaced so that the tips point between two tips on the opposite side.

The anchor tips 26 and 28 as described above advantageously provide atraumatic surfaces that may be used to grasp intralumenal tissue without causing unnecessary or undesired trauma to tissue. For example, the proximal anchors tips 26 and distal anchor tips 28 may form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the frame is deployed in-situ and expands, the movement of each loop from a delivered position to a deployed position can avoids getting caught on the papillary muscles.

The prosthesis 10 may include a valve 60. The valve 60 can be a replacement heart valve which includes a plurality of valve leaflets. The plurality of valve leaflets can function in a manner similar to the natural mitral valve, or to other valves in the vascular system. The plurality of valve leaflets can open in a first position and then engage one another to close the valve in a second position. The plurality of valve leaflets can be made to function as a one way valve such that flow in one direction opens the valve and flow in a second direction opposite the first direction closes the valve. The replacement heart valve 60 can be constructed so as to open naturally with the beating of the heart. For example, the plurality of valve leaflets can open during diastole and close during systole.

In some embodiments, the leaflets can be coupled to a valve skirt 70. For example, FIG. 1A shows a seam 62 where the proximal ends of the leaflets can be connected to the valve skirt 70.

The valve skirt 70 can be used to at least partially control how fluid flows through and/or around the valve 60. The valve skirt 70 can surround at least a portion of the valve and be connected to the valve leaflets 62. In some embodiments, the valve skirt 70 can form an inner wall connected to and positioned within the frame 20. The valve skirt 70 can also be made to move with the foreshortening portion 18 of the frame 20.

The valve skirt 70 can extend the length of the frame 20 or it can extend along only part of the length of the frame 20. In some embodiments, the ends of the heart valve 60 can coincide with ends of the valve skirt 70. In addition, one or more of the ends of the frame 20 can coincide with the ends of the valve skirt 70. In the illustrated embodiment, the proximal end of the valve skirt 70 is positioned proximally from the proximal end of the heart valve 60. The valve skirt 70 can not only extend to the distal end of the frame 20 but can also extend to the outside of the frame and is shown attached to and extending the tip 28 of each distal anchor 24. As shown, the skirt 70 is sewn to each distal anchor.

Other shapes and configurations can also be used for the valve 60 and valve skirt 70. In some embodiments, the valve skirt 70 may extend along the length of the leaflets 62, but is not connected to them. In the illustrated embodiments, the valve skirt 70 is attached to the frame 20 and the leaflets 62 are attached to the valve skirt 70.

The valve skirt 70 can be constructed in multiple different ways. The valve skirt 70 can be made of knit polyester or another stretchable or flexible fabric. In some embodiments, the valve skirt 70 is made from a material that is more flexible than the valve leaflet material. The distal and/or proximal end of the skirt 70 can be straight, curved, or have any other desired configuration. For example, the valve skirt 70 is shown with straight ends. In other embodiments the skirt distal end can be patterned to generally correspond to the undulations at the distal end 34 of the frame 20. Similarly, the proximal ends may also correspond in shape. The valve skirt 70 can be formed of one piece or multiple pieces. For example, the valve skirt 70 attached to the valve 60 can be one piece and then each distal anchor can be covered by a separate piece of material of the valve skirt 70. It is to be understood that other configurations of the valve skirt 70 can also be employed. For example, the anchors may remain uncovered, or only a portion may be covered.

In another embodiment of the valve skirt 70 the end can extend past the frame and can be wrapped around it. Thus, the valve skirt 70 can extend from the inside of the frame 20 to the outside of the frame. The skirt can extend completely around the frame for ¼, ⅓, ½, or more of the length of the distal anchors. The skirt can also cover the distal anchors 24. The skirt can be a one piece skirt, but it will be understood that the skirt can be made of multiple pieces.

The valve skirt 70, and particularly portions that cover the distal anchors 24, can beneficially be used to help prevent leakage of blood flow around the heart valve. In addition, the skirt can encourage tissue in-growth between the skirt and the natural tissue. This may further help to prevent leakage of blood flow around the heart valve.

Figure 2:
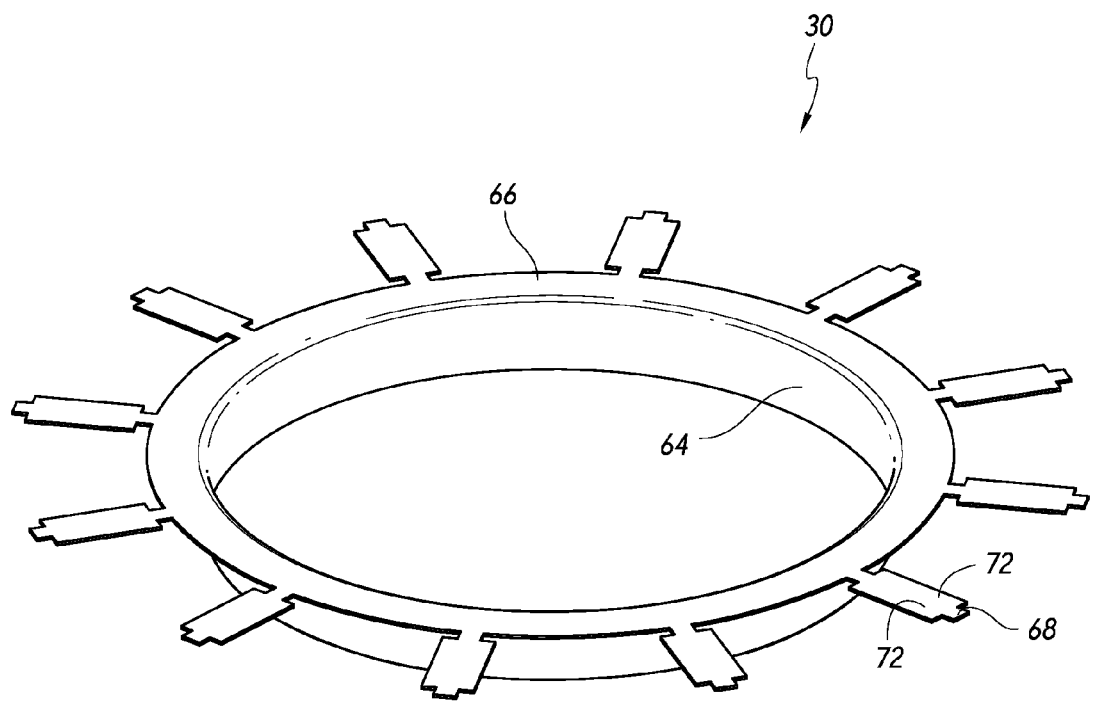
FIG. 2 is a perspective view of a skirt.

Looking to FIG. 2, an outer skirt or apron 30 is shown that may also form part of the prosthesis 10. FIG. 1A shows the outer skirt 30 attached to the frame 20. The outer skirt 30 can have a portion shaped to correspond generally with the shape of an outer portion of the frame 20. For example, a first portion 64 of the outer skirt 30 can have a cylindrical or generally cylindrical shape with an inner diameter that substantially corresponds in size to, or may be larger or slightly larger than, an outer diameter of the frame 20. In some embodiments, the first portion 64 surrounds the bulbous region of the frame and may be located surrounding the largest outer diameter of the frame 20. The outer skirt 30 can have a second portion 66 with an annular shape that extends away from the first portion 64 to an outer border with a diameter larger than the diameter of the first portion. As illustrated in FIG. 2, the second portion 66 is shown flaring outward from the first portion 64 and extending generally perpendicularly from the first portion 64. Thus, the illustrated second portion forms an annular ring comprising a proximal edge and a distal edge, wherein a diameter of the proximal edge is larger than a diameter of the distal edge.

The outer skirt 30 can attach to the frame, and more preferably attach to the anchors, in one of many different ways. The outer skirt 30 can be sewn to the frame and/or valve skirt. The outer skirt 30 can also be wrapped around a portion of the frame and then sewn to itself. In the embodiments illustrated in FIGS. 1A and 2, the second portion 66 can be attached to the proximal anchors. For example, a plurality of circumferentially spaced tabs 68 extending radially outward from the proximal edge of the second portion 66 can be used to attach the outer skirt 30 to the proximal anchors. Wings 72 on either side of the tab 68 can be wrapped around a proximal anchor and connected to each other and/or to the proximal anchor 22 to form a sleeve. The tabs 68 themselves may also form sleeves that are configured to surround at least a portion of the proximal anchors. In some embodiments, the proximal anchors 22 can include eyelets 46 that may be used to secure the skirt to the anchor. The one or both wings 72, or other parts of the tab 68, can be attached to the eyelet 46, for example by stitching the tab to the eyelet.

As shown, the eyelet 46 is spaced proximally from the end of the anchor. In other embodiments, the eyelet can be at the distal end of the anchor 22. In some embodiments, the proximal anchors can be looped anchors or have a looped end. A small tab can be passed through the looped anchor or looped end and connected to the skirt to form a loop on the skirt. Further, the outer skirt 30 may attach directly to the eyelets 46 without the need for tabs 68.

In the embodiment illustrated in FIG. 1A, the outer skirt 30 is only attached to the frame via the proximal anchors, and the first portion 64 remains unattached to any portion of the frame or any anchors. Thus, as illustrated in FIG. 1A, the first portion 64 when attached to the frame extends distally from the proximal anchors 22 and terminates in a free distal edge. In other embodiments, the first portion 64 may also be attached to portions of the frame and/or the distal anchors. Because of the bulbous shape of the frame, the free distal edge may be spaced radially outward from the frame when the frame is in an expanded configuration.

In some embodiments, the outer skirt can attach to the frame at a distal end of the skirt, or at some other location and then curve up and out towards the proximal anchors. Thus, the outer skirt may not have a distinct first portion and second portion. In still other embodiments, the outer skirt may extend along a substantial portion of the frame. The outer skirt may be attached to the distal ends of the proximal anchors and extend to the base of the anchor and then extend along the frame to a location parallel with the ends of the proximal anchors, or even more distal still, such as to the base of the distal anchors 24.

In some embodiments, the outer skirt 30 can be part of, or connected to, the valve skirt 70, such as being connected to the valve skirt 70 at or near the distal end 34 of the frame.

The outer skirt 30 can be constructed in multiple different ways and may be made of similar material to the valve skirt 70. The outer skirt 30 can be made of a layer of resilient material, such as knit polyester or another stretchable or flexible fabric. In some embodiments, the outer skirt 30 is made from a material that is more flexible than the valve leaflet material. The distal and/or proximal end of the outer skirt 30 can be straight, curved, or have any other desired configuration. The outer skirt 30 can be formed of one piece or multiple pieces. For example, the outer skirt 30 attached to the frame 20 can be one piece and then each proximal anchor 22 can be covered by a separate piece of material of the outer skirt 30. It is to be understood that other configurations of the outer skirt 30 can also be employed. For example, the anchors may remain uncovered, or only a portion may be covered.

The prosthesis 10 can also include a support band 80 as is shown in FIG. 1A. The support band 80 may be placed or positioned around or within the frame 20 at the proximal end 32. The support band 80 can be used to reinforce and/or constrain the frame 20. The support band 80 can help to control the expansion of the frame 20 from the compacted to the expanded state. The support band 80 can also be used to reduce the amount of motion that occurs at the proximal end 32 after the prosthesis 10 has been implanted at the mitral heart valve or other location.

In some embodiments, the support band 80 may comprise a polyester fabric band. The support band 80 may comprise a no-stretch or limited stretch material. Preferably the support band 80 is not made of an elastic material or a material known to have high elasticity. In some embodiments, the support band 80 is made from a material that is less flexible than the valve skirt material and/or the valve leaflet material. The distal and proximal ends of the support band 80 can be straight, curved, undulating with the undulations of frame, or any other desired configuration.

The support band 80 can be connected to the valve frame with a plurality of stitches, loops, knots, staples, or other types of connections. In some embodiments, the frame 20 can be sandwiched between two sides or layers of the support band 80. Preferably, the support band 80 is a single layer positioned within and attached to the frame 20 with a plurality of stitches around one or more of the longitudinal and/or undulating struts. In some embodiments, the support band 80 can be attached to the proximal end of the valve skirt 40.

The outer skirt 30 can beneficially prevent axial flow of fluid around an exterior of the prosthesis. For example, with the outer skirt 30 be positioned annularly around an exterior of the expandable frame and secured to at least some of the plurality of proximal anchors, the outer skirt creates an axial barrier to fluid flow exterior to the frame when deployed within a body cavity. In addition, the skirt can encourage tissue in-growth between the skirt and the natural tissue. This may further help to prevent leakage of blood flow around the heart valve.

In one embodiment, the outer skirt 30 can be used to help prevent leakage of blood flow around a heart valve, such as a mitral valve, when the prosthesis is placed in a native heart valve. For example, the outer skirt 30 can engage an atrial side of the mitral valve. The proximal anchors can also engage the mitral valve forcing the outer skirt 30 into close contact with the valve to block flow from passing through the mitral valve from outside of the frame.

Figure 3A:
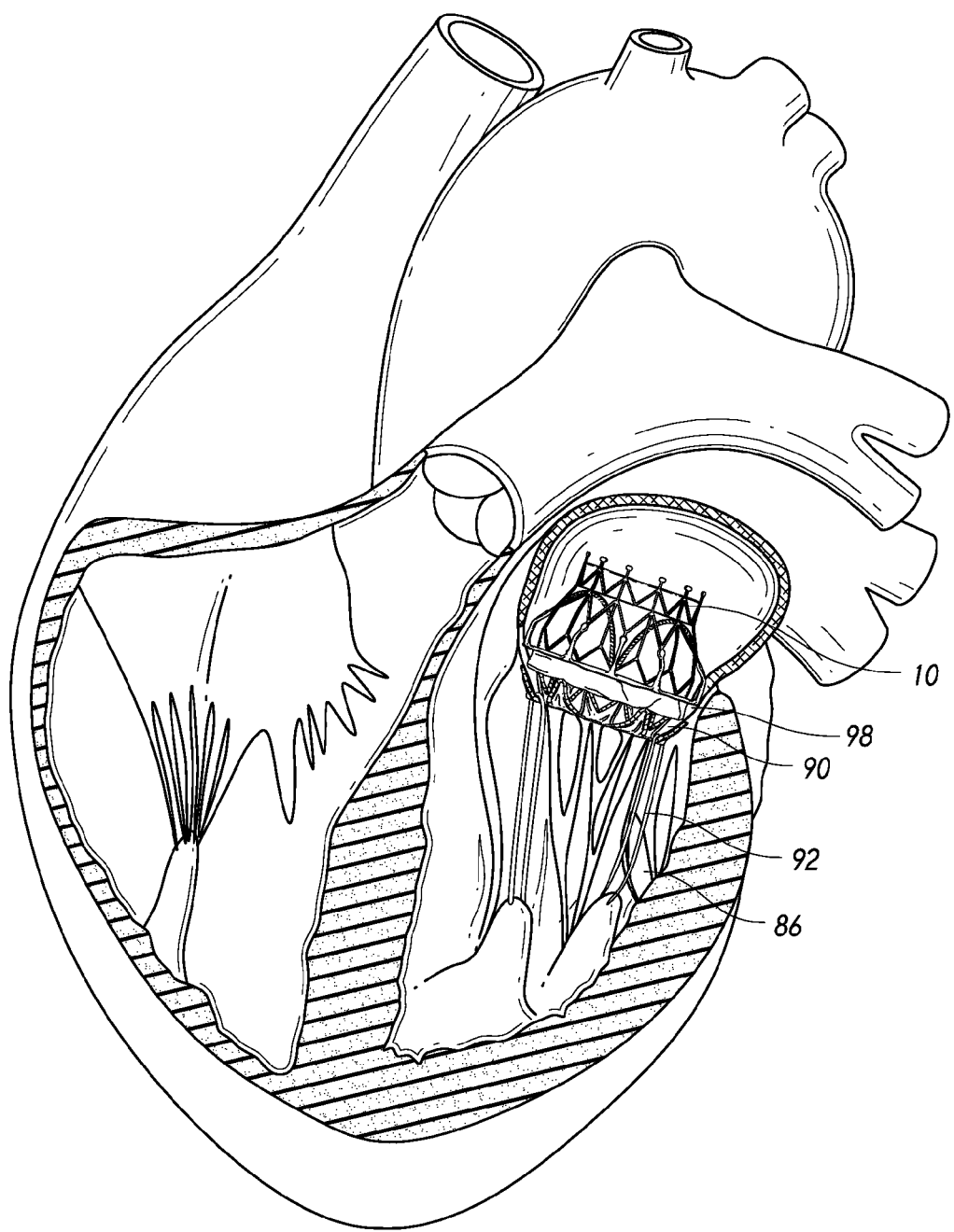
FIG. 3A is a schematic representation of a prosthesis positioned within the heart.
Figure 3B:
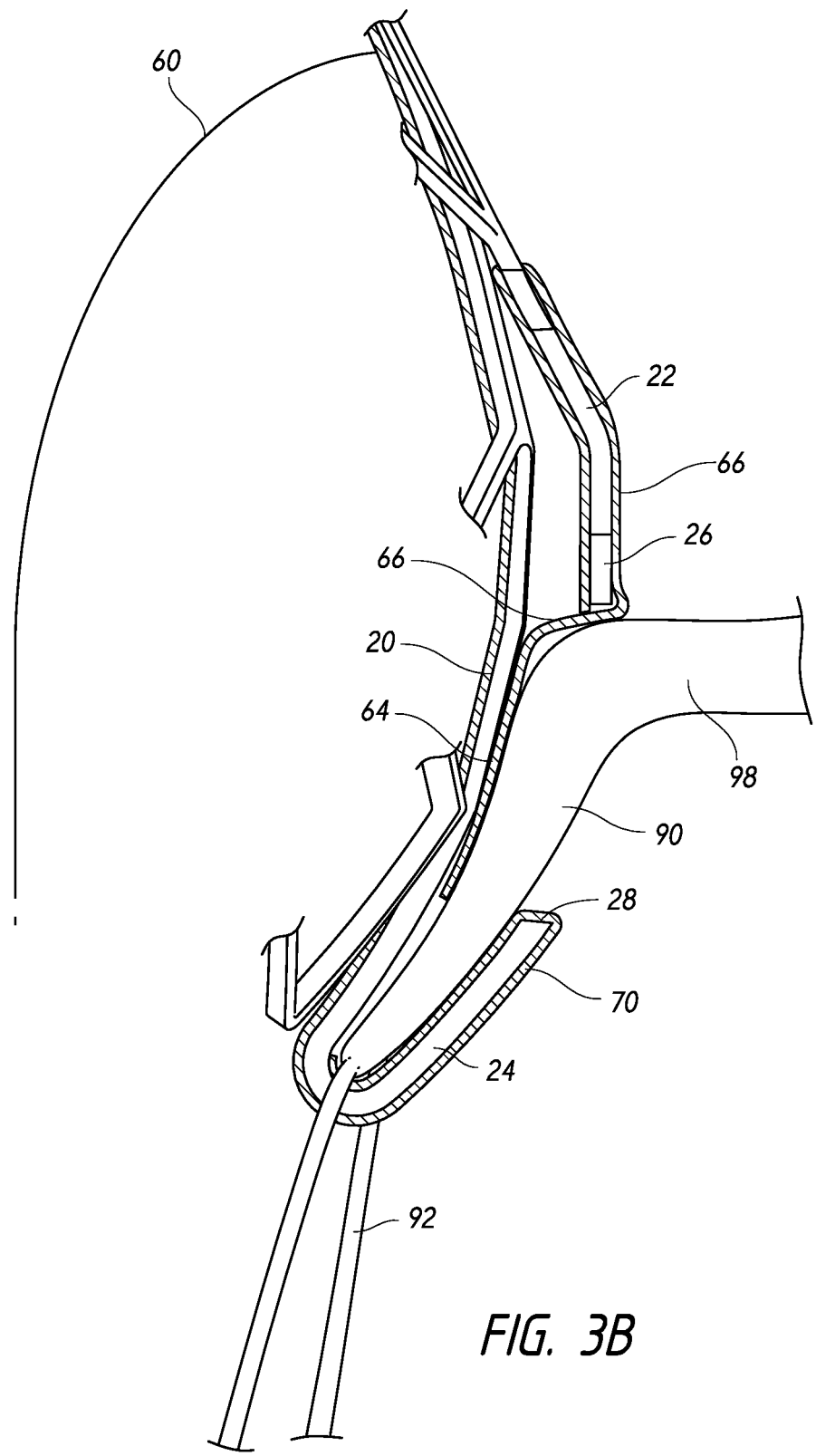
FIG. 3B is a detail schematic representation of the prosthesis positioned within the heart of FIG. 3A.

In preferred embodiments, the prostheses 10 in the form of a replacement heart such as described above may be deployed into a heart valve annulus. The prosthesis 10 may be delivered into the mitral valve in a radially compacted or collapsed configuration and positioned when compacted so that the anchor tips 26, 28 of the opposing anchors 22, 24 are disposed on opposite sides of the native annulus 98 as shown in FIGS. 3A and 3B. As the replacement heart valve 10 is expanded, the opposing anchors are drawn closer together and may grasp tissue on opposite sides of the native annulus 98 and securely hold the replacement heart valve 10 in position. As such, the replacement heart valve 10 can be held securely in position without requiring a substantial radial force against the native annulus. Because the anchor tips are preferably atraumatic, the grasping or engaging of tissue by the prosthesis minimizes damage to the native tissue. The foreshortening portion 18 can be used to move the anchor tips 26, 28 closer together as the replacement heart valve 10 moves to the expanded position to thereby engage the native valve annulus. The prosthesis can be deployed into a heart valve or otherwise deployed in manners similar to those described with respect to a replacement heart valve in U.S. Publication Nos. 2010/0298931 and 2012/0078353 the entireties of each of which are hereby incorporated by reference and made a part of this specification.

FIGS. 3A and 3B show a schematic representation of the replacement heart valve 10 installed in a human heart 84. The heart is shown in cross-section, and represents typical anatomy, including a left atrium 78 and left ventricle 86. The left atrium 78 and left ventricle 86 communicate with one another through a mitral annulus 98. Also shown schematically is a native anterior mitral leaflet 90 having chordae tendineae 92 that connect a downstream end of the anterior mitral leaflet 90 and to the left ventricle 86.

In one preferred embodiment, a method is provided of delivering a replacement valve to a native mitral valve and atraumatically securing the replacement valve relative to the native mitral valve annulus 98. The replacement valve can be mounted on a delivery device and delivered to the native mitral valve annulus while the replacement valve is in a radially compacted state. The replacement valve may be positioned so that the ends or tips of the distal anchors are on a ventricular side of the native leaflets 90 beyond a location where chordae tendineae 92 connect to free ends of the native leaflets. At least a portion of the replacement valve can be released from the delivery device to thereby expand the distal anchors radially outwardly. At this time the distal anchors may extend between at least some of the chordae. The distal anchors (along with the frame) can be moved toward the ventricular side of the native valve annulus with the distal anchors extending between at least some of the chordae tendineae to provide tension on the chordae tendineae. With tension provided on the chordae tendineae, the replacement valve can be further released from the delivery device to thereby expand the proximal anchors radially outwardly. The proximal anchors upon further release of the replacement valve from the delivery device can move into engagement with tissue on an atrial side of the native valve annulus, such as with the atrial side of the native valve annulus.

The method just described may utilize any of the prostheses herein described, including any of the prostheses described in the patents and applications incorporated by reference herein. In one embodiment, a prosthesis where the ends of the distal anchors are not positioned as far out radially as the ends of the proximal anchors when the frame is expanded can beneficially be used in this method. Thus, the distal anchors may have a suitable length for extending between and providing tension on the chordae tendineae, but need not and may in some embodiments not engage tissue with the tips 28. Thus, in some embodiments the some or all of the distal anchors remain spaced from tissue on the ventricular side of the native valve annulus after delivery and expansion. The interaction between the distal anchors and the chordae tendineae may therefore be sufficient to secure the distal end of the prosthesis, while the engagement of the proximal anchors with tissue on the atrial side of the native valve annulus will help further secure and orient the prosthesis As illustrated in FIGS. 3A and 3B, the distal anchors may comprise loops, such as any of the looped structures previously described or described in the patents and applications incorporated by reference herein. The proximal and/or distal anchors may also be covered with a resilient material such as described above for the outer skirt 30 and valve skirt 70 that promotes tissue growth with adjacent body tissue. Such material may also be useful to prevent paravalvular leakage. The atraumatic distal anchors may advantageously prevent snagging of the prosthesis on internal structures, such as the papillary muscles.

When the prosthesis is in an expanded configuration within the native mitral heart valve, the engagement of the proximal anchors 22 with tissue on the atrial side of the native mitral valve causes at least the second portion 66 of the outer skirt 30 to also engage the tissue on the atrial side of the native mitral valve. The first portion 64 of the outer skirt extends distally from the proximal anchors toward the ventricle. Because the diameter of the first portion 64 is close or the same in dimension as the frame, at least at the proximal edge of the first portion 64, the outer skirt form a barrier to blood flow around the outside or external to the frame. The outer skirt 30 can be forced against the outside of the frame 20 by the native leaflets. Where the native leaflets do not force the outer skirt 30 against the frame, or where the contact is not as strong, the outer skirt 30 is still present to block, or impede blood flow. It will be understood that having multiple contact points between the native valve and the outer skirt can allow the outer skirt to securely cover areas where there are fewer contacts between the two. As described above, the outer skirt may also promote tissue growth with tissue that it contacts.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A prosthesis configured to grasp intralumenal tissue when deployed within a body cavity and prevent axial flow of fluid around an exterior of the prosthesis, the prosthesis comprising:
   an expandable frame comprising a proximal end and a distal end and a longitudinal axis extending therethrough, the frame configured to radially expand and contract for deployment within the body cavity;
   a plurality of anchors each connected to the frame so that when the frame is in an expanded configuration an end of each anchor is positioned radially outward from the frame, the plurality of anchors comprising a plurality of distal anchors having ends which extend proximally when the frame is in an expanded configuration, the ends of the distal anchors being circumferentially spaced apart such that at least one of the plurality of distal anchors is configured to extend between chordae tendineae when the frame is in an expanded configuration; and
   a skirt annularly positioned around an exterior of the expandable frame to create an axial barrier to fluid flow exterior to the frame when deployed within the body cavity, the skirt comprising:
      a first portion having a proximal end and a distal end, the proximal end being positioned at a location spaced between the proximal and distal ends of the frame and being unattached to the frame or plurality of anchors, the distal end of the first portion being positioned closer to the distal end of the frame than the proximal end of the first portion; and
      a second portion shaped to extend radially outward from the frame at a location spaced between the proximal end and the distal end to prevent axial flow of fluid around an exterior of the prosthesis, the second portion shaped to extend radially from a proximal end of the first portion;
   wherein when the frame is in an expanded configuration, the frame has a larger cross-sectional dimension in a middle portion of the frame and a smaller cross-sectional dimension in a proximal portion and a distal portion of the frame, and wherein the ends of the anchors are positioned radially outward from the middle portion of the frame.

2. The prosthesis of claim 1, wherein the skirt comprises a plurality of wings or sleeves that surround at least some of the anchors.

3. The prosthesis of claim 1, wherein at least some of the plurality of anchors comprise looped ends, and the skirt is attached to the looped ends.

4. The prosthesis of claim 1, wherein the plurality of anchors comprise a plurality of proximal anchors having ends which extend distally when the frame is in an expanded configuration, wherein the ends of the proximal anchors are axially spaced from the ends of the distal anchors when the frame is in an expanded configuration.

5. The prosthesis of claim 4, wherein the skirt is secured to at least some of the proximal anchors.

6. The prosthesis of claim 5, wherein the skirt extends distally from the ends of the proximal anchors to a free distal edge.

7. The prosthesis of claim 4, wherein the second portion of the skirt is configured to extend radially outward from the frame between ends of the proximal and distal anchors.

8. The prosthesis of claim 4, wherein the plurality of proximal anchors are integrally formed with the frame.

9. The prosthesis of claim 1, further comprising a second skirt covering distal anchors to facilitate in-growth of adjacent tissue when the prosthesis is deployed within a body cavity.

10. The prosthesis of claim 1, further comprising a valve body attached to the frame.

11. The prosthesis of claim 1, wherein the proximal end and the distal end have substantially the same cross-sectional dimension.

12. A replacement heart valve suitable for use for securement to a native mitral valve annulus, comprising the prosthesis of claim 1.

13. The prosthesis of claim 12, wherein the middle portion of the frame is configured to engage tissue of a native mitral valve.

14. The prosthesis of claim 1, wherein the second portion of the skirt is configured to extend radially outward from the middle portion of the frame.

15. The prosthesis of claim 1, wherein the first portion of the skirt is configured to surround a middle portion of the frame, the middle portion of the frame being configured to engage intalumenal tissue.

16. A prosthesis configured to grasp intralumenal tissue when deployed within a body cavity and prevent axial flow of fluid around in exterior of the prosthesis, the prosthesis comprising:
an expandable frame comprising a proximal end and a distal end and a longitudinal axis extending therethrough, the frame configured to radially expand and contract for deployment within the body cavity;
a distal anchoring portion connected to the frame so that when the frame is in an expanded configuration an end of the distal anchoring portion is positioned radially outward from the frame, the distal anchoring portion comprising a plurality of distal anchors comprising circumferentially spaced apart ends; and
a skirt annularly positioned around an exterior of the expandable frame to create an axial barrier to fluid flow exterior to the frame when deployed within the body cavity, the axial barrier being positioned at least proximally of the end of the distal anchoring portion, the skirt comprising:
a first portion having a proximal end and a distal end, the distal end of the first portion being positioned more distal than the end of the distal anchoring portion; and
a second portion shaped to extend radially outward from the frame at a location spaced between the proximal end and the distal end to prevent axial flow of fluid around an exterior of the prosthesis;
wherein when the frame is in an expanded configuration:
a cross-sectional dimension of the proximal end of the frame;
the distal end of the frame and the proximal end have different cross-sectional dimensions, and
the ends of the anchors are positioned radially outward from the middle portion of the frame.

17. The prosthesis of claim 16, the prosthesis comprising a proximal anchoring portion connected to the frame so that when the frame is in an expanded configuration an end of the proximal anchoring portion is positioned radially outward from the frame.

18. The prosthesis of claim 17, wherein the proximal anchoring portion comprises a plurality of proximal anchors and wherein the plurality of proximal anchors and the plurality of distal anchors are circumferentially staggered.

19. The prosthesis of claim 16, wherein at least some of the plurality of distal anchors are sized to extend between at least some of the chordae tendineae.

20. The prosthesis of claim 16, wherein the distal end of the first portion is positioned at a base of the distal anchoring portion.

21. The prosthesis of claim 16, wherein the distal anchoring portion comprises at least six distal anchors.

22. A prosthesis configured to grasp intralumenal tissue when deployed within a native mitral valve and prevent axial flow of fluid around in exterior of the prosthesis, the prosthesis comprising:
an expandable frame comprising a proximal end and a distal end and a longitudinal axis extending therethrough, the frame configured to radially expand and contract for deployment within the native mitral valve;
a proximal anchoring portion sized to contact an atrial side of a native mitral valve annulus when the prosthesis is deployed within the native mitral valve, the proximal anchoring portion being connected to the frame at a location distal of the proximal end of the frame, wherein the proximal anchoring portion extends radially outward from the frame when the frame is in an expanded configuration;
a distal anchoring portion sized to be positioned on a ventricular side of the native mitral valve annulus when the prosthesis is deployed within the native mitral valve, the distal anchoring portion comprising a plurality of spaced apart distal anchors extending towards a proximal end of the expandable frame, wherein the distal anchors are positioned radially outward from the frame when the frame is in an expanded configuration; and
a skirt disposed along an exterior of the prosthesis to create an axial barrier to fluid flow exterior to the prosthesis when deployed within the native mitral valve, the skirt comprising:
a generally cylindrical portion extending along an exterior of the frame, wherein a proximal end of the generally cylindrical portion is positioned distally of the proximal end of the frame and a distal end of the generally cylindrical portion is positioned proximally of the distal anchors; and
a ring portion sized to contact an atrial side of a native mitral valve annulus when the prosthesis is expanded and deployed within the native mitral valve, the ring portion extending radially outward from the frame at the proximal end of the generally cylindrical portion, wherein at least a portion of the ring portion extends along the proximal anchoring portion;
wherein when the frame is in an expanded configuration a cross-sectional dimension in a middle portion of the frame is larger than a cross-sectional dimension of the proximal end of the frame.

23. The prosthesis of claim 22, wherein the expandable frame comprises a foreshortening portion having a plurality of cells and wherein the skirt has an axial dimension less than two cell lengths.

24. The prosthesis of claim 22, wherein the generally cylindrical portion of the skirt is configured to contact the expandable frame along a first surface and tissue of the native mitral valve along a second surface to create an axial barrier to fluid flow exterior to the prosthesis when deployed within the native mitral valve.

25. The prosthesis of claim 22, wherein an inner diameter of the generally cylindrical portion of the skirt substantially corresponds in size to an outer diameter of the frame along which the generally cylindrical portion extends.

* * * * *